(12) United States Patent
Stern et al.

(10) Patent No.: US 6,759,549 B2
(45) Date of Patent: *Jul. 6, 2004

(54) METHOD OF PREPARING AMINO CARBOXYLIC ACIDS

(75) Inventors: Michael K. Stern, Clayton, MO (US); Todd J. Johnson, Boonville, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/408,515

(22) Filed: Apr. 7, 2003

(65) Prior Publication Data

US 2003/0225298 A1 Dec. 4, 2003

Related U.S. Application Data

(60) Continuation of application No. 10/151,650, filed on May 20, 2002, now abandoned, which is a division of application No. 09/871,829, filed on Jun. 1, 2001, now abandoned, which is a division of application No. 09/499,699, filed on Feb. 7, 2000, now Pat. No. 6,265,605, which is a division of application No. 09/022,967, filed on Feb. 12, 1998, now Pat. No. 6,153,753.

(60) Provisional application No. 60/037,775, filed on Feb. 13, 1997.

(51) Int. Cl.[7] .......................... C07F 9/22; C07C 229/00
(52) U.S. Cl. ......................................... 562/14; 562/565
(58) Field of Search .................... 562/14, 565

(56) References Cited

U.S. PATENT DOCUMENTS

| | | | |
|---|---|---|---|
| 1,532,329 A | 4/1925 | McConnell | |
| 2,559,835 A | 7/1951 | Zerner et al. | |
| 2,757,200 A | 7/1956 | Jones et al. | |
| 2,757,204 A | 7/1956 | Ratcliff | |

(List continued on next page.)

FOREIGN PATENT DOCUMENTS

| | | |
|---|---|---|
| DE | 27 19 583 | 11/1977 |
| EP | 0 145 265 A2 | 6/1985 |
| EP | 0 170 830 A1 | 2/1986 |
| EP | 0 197 659 A1 | 10/1986 |
| EP | 0 207 580 A1 | 1/1987 |
| EP | 0 263 624 A2 | 4/1988 |
| EP | 0 281 707 A2 | 9/1988 |
| EP | 0 315 716 A1 | 5/1989 |
| EP | 0 413 068 A1 | 2/1991 |
| EP | 0 680 948 A1 | 11/1995 |
| GB | 1 410 722 | 10/1975 |
| GB | 2 252 770 A | 8/1992 |
| HU | 170157 B | 4/1977 |
| HU | 173170 B | 3/1978 |
| IR | 44829 | 4/1982 |

OTHER PUBLICATIONS

CAS printout for Nachev et al. Chem. Abs. 117:70275.*

Bartha, F., et al. "Plant Growth Regulator Precursors Comprising N–(phosphonomethyl) glycine of its Derivative and Carbonates" Chemical Abstract, vol. 113, No. 36393 (1989).

(List continued on next page.)

*Primary Examiner*—Richard L. Raymond
*Assistant Examiner*—Hong Liu
(74) *Attorney, Agent, or Firm*—Senniger, Powers, Leavitt & Roedel; Joseph A. Schaper

(57) ABSTRACT

Novel compounds, N,N'-bis(phosphonomethyl)-N,N'-bis (hydroxycarbonylmethyl)urea and N,N,N',N'-tetrakis (hydroxycarbonylmethyl)urea, suitable for use in preparing N-acyl aminocarboxylic acids that can be readily converted to N-(phosphonomethyl)glycine are provided. The compounds may be formed by the reaction of bis-(phosophonomethyl)urea or urea respectively with carbon monoxide and formaldehyde in the presence of a carboxymethylation catalyst precursor and solvent.

3 Claims, 3 Drawing Sheets

U.S. PATENT DOCUMENTS

| | | | |
|---|---|---|---|
| 2,757,205 A | 7/1956 | Mertzweiller et al. | |
| 2,757,206 A | 7/1956 | Jones et al. | |
| 3,260,745 A | 7/1966 | Andress, Jr. et al. | |
| 3,288,846 A | 11/1966 | Irani et al. | |
| 3,585,019 A | 6/1971 | Hays | |
| 3,766,266 A | 10/1973 | Wakamatsu et al. | |
| 3,904,668 A | 9/1975 | Gaudette et al. | |
| 3,954,750 A | 5/1976 | Coon | |
| 3,991,095 A | 11/1976 | Gaertner et al. | |
| 4,191,552 A | 3/1980 | Large et al. | |
| 4,197,254 A | 4/1980 | Gaertner | |
| 4,264,515 A | 4/1981 | Stern et al. | |
| 4,312,662 A | 1/1982 | Gaertner | |
| 4,328,027 A | 5/1982 | Buren et al. | |
| 4,400,330 A | 8/1983 | Wong et al. | |
| 4,533,500 A | 8/1985 | Chauvin et al. | |
| 4,624,937 A | 11/1986 | Chou | |
| 4,657,705 A | 4/1987 | Miller et al. | |
| 4,696,772 A | 9/1987 | Chou | |
| 4,918,222 A | 4/1990 | Lin et al. | |
| 4,954,466 A | 9/1990 | Weisenfeld | |
| 5,068,404 A | 11/1991 | Miller et al. | |
| 6,265,605 B1 * | 7/2001 | Johnson et al. | 562/14 |

OTHER PUBLICATIONS

Chai, C., et al., "Reactivities of Piperazine–2,5–diones in Radical Bromination Reactions" Chemical Abstract, vol. 126, No. 157470 (1996).

Dapperheld, S., et al. "Organic Electron Transfer Systems. II. Substituted Triarylamine Cation–Radical Redox Sytems–Synthesis, Electrochemical and Spectroscopic Properties. Hammet Behavior, and Suitability as Redox Catalysts" Chem. Ber., vol. 124, No. 11 (1991) pp. 2557–2567. (Abstract Only).

Dolphin, D., et al. "Polyhaloporphyrins: Unusual Ligands for Metals and Metal–Catalyzed Oxidations" Accounts of Chemical Research, vol. 30, No. 6 (1997) pp. 251–259.

Dorfman, A., et al. "Kinetics and Mechanism of the Oxidative Alkoxylation of Tetraphosphorus in the Presence of Copper (II) Sulfates and Carboxylates" Kinetics and Catalysis, vol. 36, No. 1 (1995) pp. 93–100.

Fernandez, A., et al. "Improved Synthesis of Symmetrical N,N'–alkylidene bisamides" Chemical Abstracts, vol. 126, No. 18441 (1996).

Franz, J., et al. "Methods of Preparing Glyphosate" Glyphosate: A Unique Global Herbicide, Chapter 8 (1997) American Chemical Society, Washington, D.C., pp. 233–262.

Furhop, J., "Reversible Reactions of Porphyrins and Metalloporphyrins and Electrochemistry" Porphyrins and Metalloprophyrins, Chapter 14, (1975) Elsevier Scientific Publishing Company Amsterdam, The Netherlands, pp. 593–623.

Ladhar, F., et al.., "Synthesis of 1, 3, 5–Triacylperhydro–1,3,5–triazines Catalyzed By Ion–Exchange Resins", Chemical Abstracts, vol. 107, No. 9, 1987.

Ladhar, F., et al. Chemical Abstracts, vol. 107, No. 9, Aug. 31, 1987, Columbus, Ohio; Abstract No. 77759, Synthesis of 1,3,5–triacylperhydro–1,3,5–triazines catalyzed by ion–exchange resins XP002133494 & Synthesis (1986), 8, 643–4.

Masui, M., et al. "N–Hydroxyphthaliide as an Effective Mediator for the Oxidation of Alcohols by Electrolysis" J. Chemical Society, Chemical Communications (1983) pp. 479–480.

Nachev, I., "Synthesis and Enzyme–substrate Interactions of N–phosphonomethylglycine and N–[(hydroxymethylphosphinyl)methyl]glycine" Chemical Abstracts, vol. 113, No. 147151 (1989).

Natangelo, M., et al. "GC–MS Analysis of N–phosphonomethylglycine(glyphosate) Samples Through Derivatization with a Perfluoroanhydride and Trifluoroethanol" Chemical Abstracts, vol. 120, No. 25500 (1993).

Parnaud, J., et al. "Some Aspects of the Catalytic Synthesis of N–acyl–α–Aminoacids by Carbonylation of Aldehydes in the Presence of Amides" Journal of Molecular Catalysis, vol. 6 (1979) pp. 341–350.

Perichon, J., "Miscellaneousl Hydrocarbons" Encyclopedia of Electrochemistry of the Elements, vol. XI (1978) Marcel Dekker, Inc., New York, pp. 163–166.

Petrovanu, O., et al. "IR Spectral Characteristics of Some Diacylmethylenediamine Type Derivatives" Chemical Abstract, vol. 96, No. 34350 (1980).

Riley, D., et al. "Vanadium (IV, V) Salts as Homogeneous Catalysts for the Oxygen Oxidation of N–(phosphonomethyl)iminodiacetic acid to N–(phosphonomethyl)glycine" Chemical Abstract, vol. 115, No. 232353 (1991).

Senmelhack, M., et al., "Nitroxyl–Mediated electrooxidation of Alcohols to Aldehydes and Ketones" J. Am. Chem. Soc., vol. 105, No. 13 (1983) pp. 4492–4494.

Wakamatsu, H., et al, "Synthesis of N–Acyl Amino–Acids by a Carbonylation Reaction" Chemical Communications (1971), pp. 1540.

Weisenfeld, R., "Metal–Catalyzed Carbonylation of Acetamide: Homogeneous–Phase Recovery of Cobalt from a Water–Soluble Amino Acid" Ind. Eng. Chem. Res., vol. 31, No. 2 (1992) pp. 636–638.

Beilstein Information Service; File: XFIRE, XP002133493, 1988.

Beilstein Information Service, File: XFIRE, XP002133493, Beilstein Registry Nos. 290227, 371355, 824030, 5997944 and 6071065, 1988–1999.

Chemical Abstract Entry: RN 13547–17–6.

International Search Report No. WO 98/35930.

International Search Report from the Hungarian Patent Office dated Nov. 14, 2001.

Supplemental European Search Report for European Application No. 98907465.3, Mar. 31, 2000.

* cited by examiner

METHOD OF PREPARING AMINO CARBOXYLIC ACIDS

CROSS-REFERENCE TO RELATED APPLICATIONS

This application is a continuation of U.S. Ser. No. 10/151,650, filed May 20, 2002, now ABN, which is a divisional of U.S. Ser. No. 09/871,829, filed Jun. 1, 2001, now abandoned, which is a divisional of U.S. patent application Ser. No. 09/499,699, filed Feb. 7, 2000, now U.S. Pat. No. 6,265,605, which is a divisional of U.S. Ser. No. 09/022,967, filed Feb. 12, 1998, now U.S. Pat. No. 6,153,753, which claims the benefit of U.S. Provisional Application Serial No. 60/037,775, filed Feb. 13, 1997. The complete texts of these related applications are incorporated herein by reference.

BACKGROUND OF THE INVENTION

1. Field of the Invention

The present invention relates, in general, to the preparation of amino carboxylic acids, salts, and esters, and, in a preferred embodiment, to the preparation of N-(phosphonomethyl)glycine, its salts, and its esters, wherein the method of preparation comprises a carboxymethylation step.

2. Description of Related Art

Amino carboxylic acids are useful in various applications. Glycine, for example, is widely used as an additive in processed meat, beverages, and in other processed food stuffs. It is also used widely as a raw material for pharmaceuticals, agricultural chemicals, and pesticides. N-(phosphonomethyl)glycine, also known by its common name glyphosate, is a highly effective and commercially important herbicide useful for combating the presence of a wide variety of unwanted vegetation, including agricultural weeds. Between 1988 and 1991, approximately 13 to 20 million acres per year worldwide were treated with glyphosate, making it one of the most important herbicides in the world. Convenient and economical methods of preparing glyphosate and other amino carboxylic acids are, therefore, of great importance.

Franz, et al. in *Glyphosate: A Unique Global Herbicide* (ACS Monograph 189, 1997) at p. 233–257 identify a number of routes by which glyphosate can be prepared. According to one of these, iminodiacetic acid disodium salt (DSIDA) is treated with formaldehyde and phosphorous acid or phosphorous trichloride to produce N-(phosphonomethyl)-iminodiacetic acid and sodium chloride. A carboxymethyl group on the N-(phosphonomethyl) iminodiacetic acid is then oxidatively cleaved in the presence of a carbon catalyst to produce glyphosate acid. A significant drawback of this method is that it produces as a side product three equivalents of sodium chloride per equivalent of glyphosate. Sodium chloride streams of this nature are difficult to recycle because typically after precipitation the salt contains significant quantities of entrapped organic matter. Such entrapped organic matter prevents the sodium chloride from being used for many purposes, for example in foods or feed. Further recrystallization of the sodium chloride adds cost which makes recycle economically unfeasible. Alternate methods of disposing of sodium chloride without detriment to the environment are expensive and difficult.

Franz et al. (at 242–243) describe another method in which N-isopropylglycine is phosphonomethylated to produce N-isopropyl-N-(phosphonomethyl)glycine. In this method, the N-isopropyl-N-(phosphonomethyl)glycine is heated to 300° C. with 50% sodium hydroxide and then treated with hydrochloric acid to produce glyphosate. The severe and costly conditions necessary to cleave the N-isopropyl group represents a significant disadvantage of that method. In addition, this method also produces a significant sodium chloride waste stream.

In U.S. Pat. No. 4,400,330, Wong discloses a method for the preparation of glyphosate in which 2,5-diketopiperazine is reacted with paraformaldehyde and a phosphorous trihalide in a carboxylic acid solvent to produce N,N'-di(phosphonomethyl)-2,5-diketopiperazine. The product is then saponified to form a glyphosate sodium salt. The Wong method is limited by the fact diketopiperazine is a relatively expensive starting material. Furthermore, the conversion of glyphosate sodium salt to the acid form or to other salts produces an undesired sodium chloride waste stream.

SUMMARY OF THE INVENTION

Among the objects of the present invention, therefore, is the provision of a well-defined, low-cost process for the production of amino carboxylic acids, in general, and N-(phosphonomethyl)glycine, in particular, and the provision of such a process in which sodium chloride is not generated as a by-product.

In the process of the present invention, an N-acyl amino carboxylic acid is formed via a carboxymethylation reaction. In this reaction, a reaction mixture is formed which contains a base pair, carbon monoxide and an aldehyde with the base pair being derived from a carbamoyl compound and a carboxymethylation catalyst precursor. In a preferred embodiment, the carbamoyl compound and aldehyde are selected to yield an N-acyl amino carboxylic acid which is readily converted to N-(phosphonomethyl)glycine, or a salt or ester thereof having the following structure:

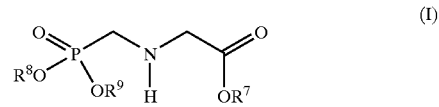
(I)

wherein $R^7$, $R^8$, and $R^9$ independently are hydrogen, hydrocarbyl, substituted hydrocarbyl, or an agronomically acceptable cation. In general, carbamoyl compounds which are selected to produce N-(phosphonomethyl)glycine correspond to structure (II):

(II)

wherein $R^1$ is hydrogen, hydrocarbyl, substituted hydrocarbyl, $-NR^3R^4$, $-OR^5$, or $-SR^6$;

$R^2$ and $R^{2a}$ are independently hydrogen, hydrocarbyl, or substituted hydrocarbyl;

$R^3$ and $R^4$ are independently hydrogen, hydrocarbyl, or substituted hydrocarbyl; and $R^5$ and $R^6$ are independently hydrogen, hydrocarbyl, substituted hydrocarbyl, or a salt-forming cation;

provided, however, (1) at least one of $R^2$ and $R^{2a}$ is hydrogen, hydroxymethyl, amidomethyl, or another substituent which, under the carboxymethylation reaction conditions, is capable of producing an N—H bond, or (2) $R^1$ is —NR³R⁴ and at least one of R³ and R⁴ is hydrogen, hydroxymethyl, amidomethyl, or another substituent which, under the carboxymethylation reaction conditions, is capable of producing an N—H bond.

In one embodiment of the process of the present invention, therefore, an amino carboxylic acid or a salt or an ester thereof is prepared by carboxymethylation of a carbamoyl compound. In this process, a reaction mixture is formed by combining the carbamoyl compound and a carboxymethylation catalyst precursor in the presence of carbon monoxide and hydrogen. Water and an aldehyde are introduced into the reaction mixture after the carbamoyl compound and the carboxymethylation catalyst precursor are combined and the components of the reaction mixture are reacted to generate a product mixture containing an N-acyl amino carboxylic acid reaction product and a catalyst reaction product.

In another embodiment of the process of the present invention, a reaction mixture containing the carbamoyl compound, carbon monoxide, hydrogen, an aldehyde, and a carboxymethylation catalyst precursor derived from cobalt is formed. The components of the reaction mixture are reacted to generate a product mixture containing an N-acyl amino carboxylic acid reaction product and a catalyst reaction product. The catalyst reaction product is recovered from the product mixture and the catalyst reaction product is regenerated in the presence of the carbamoyl compound.

In a further embodiment, the process of the present invention is directed to the preparation of N-(phosphonomethyl)glycine or a salt or ester thereof. In this process, an N-acyl amino acid reaction product is prepared by carboxymethylating a carbamoyl compound in a reaction mixture formed by combining the carbamoyl compound, formaldehyde, carbon monoxide, hydrogen and a carboxymethylation catalyst precursor derived from cobalt. The N-acyl amino acid reaction product is converted to N-(phosphonomethyl)glycine or a salt or ester thereof wherein said conversion comprises deacylating the N-acyl amino acid reaction product to generate a carboxylic acid and an amino acid. The carboxylic acid is reacted with an amine to generate the carbamoyl compound or a compound from which the carbamoyl compound may be derived.

In a further embodiment, N-(phosphonomethyl)glycine or a salt or ester thereof is derived from N-acetyliminodiacetic acid. The N-acetyliminodiacetic acid is prepared by carboxymethylating acetamide in a reaction mixture formed by combining acetamide, acetic acid, water, formaldehyde, carbon monoxide, hydrogen, and a carboxymethylation catalyst precursor derived from cobalt. The N-acetyliminodiacetic acid is converted to N-(phosphonomethyl)glycine or a salt or ester thereof wherein said conversion comprises deacylating N-acetyliminodiacetic acid.

In a further embodiment, N-(phosphonomethyl)glycine or a salt or ester thereof is derived from an N-acyl amino acid carboxylic acid reaction product which is prepared from a reaction mixture containing a carbamoyl compound selected from among ureas and N-alkyl substituted amides, a carboxymethylation catalyst precursor, formaldehyde, and carbon monoxide. The N-acyl amino carboxylic acid reaction product is then converted to N-(phosphonomethyl)glycine or a salt or ester thereof. If the carbamoyl compound is an N-alkyl substituted amide, the conversion step(s) comprise oxidatively dealkylating the N-acyl amino carboxylic acid reaction product in the presence of oxygen using a noble metal catalyst.

The present invention is additionally directed to the certain key starting materials used and intermediates prepared in the process of the present invention.

For example, in one embodiment, the present invention is directed to a compound having the formula:

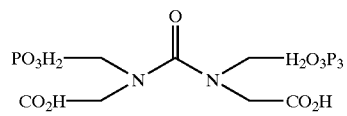

In another embodiment, the present invention is directed to a compound having the formula:

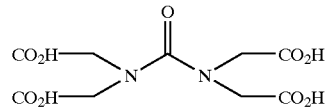

In yet another embodiment, the present invention is directed to an acetamide equivalent compound selected from the group consisting of compounds having the formula:

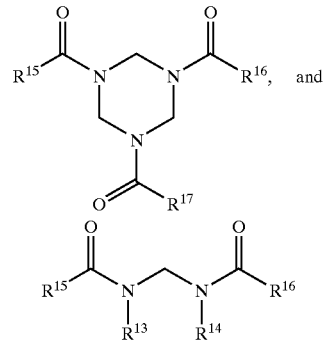

wherein $R^{13}$ and $R^{14}$ are independently hydrogen, hydroxymethyl, alkyl, carboxymethyl, phosphonomethyl, or an ester or salt of carboxymethyl or phosphonomethyl; $R^{15}$, $R^{16}$ and $R^{17}$ are independently alkyl or —NR³R⁴; and $R^3$ and $R^4$ are independently hydrogen, hydrocarbyl, or substituted hydrocarbyl.

In still a further embodiment, the present invention is directed to a compound having the formula:

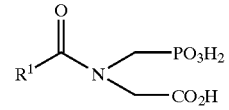

wherein $R^1$ is hydrogen, hydrocarbyl, substituted hydrocarbyl, —NR³R⁴, or SR⁶; $R^3$ and $R^4$ are independently hydrogen, hydrocarbyl, or substituted hydrocarbyl; and $R^6$ is hydrogen, hydrocarbyl, substituted hydrocarbyl, or a salt-forming cation.

Further scope of the applicability of the present invention will become apparent from the detailed description provided below. It should be understood, however, that the following detailed description and examples, while indicating preferred embodiments of the invention, are given by way of illustration only since various changes and modifications within the spirit and scope of the invention will become apparent to those skilled in the art from this detailed description.

DETAILED DESCRIPTION OF THE INVENTION

Figure 1:
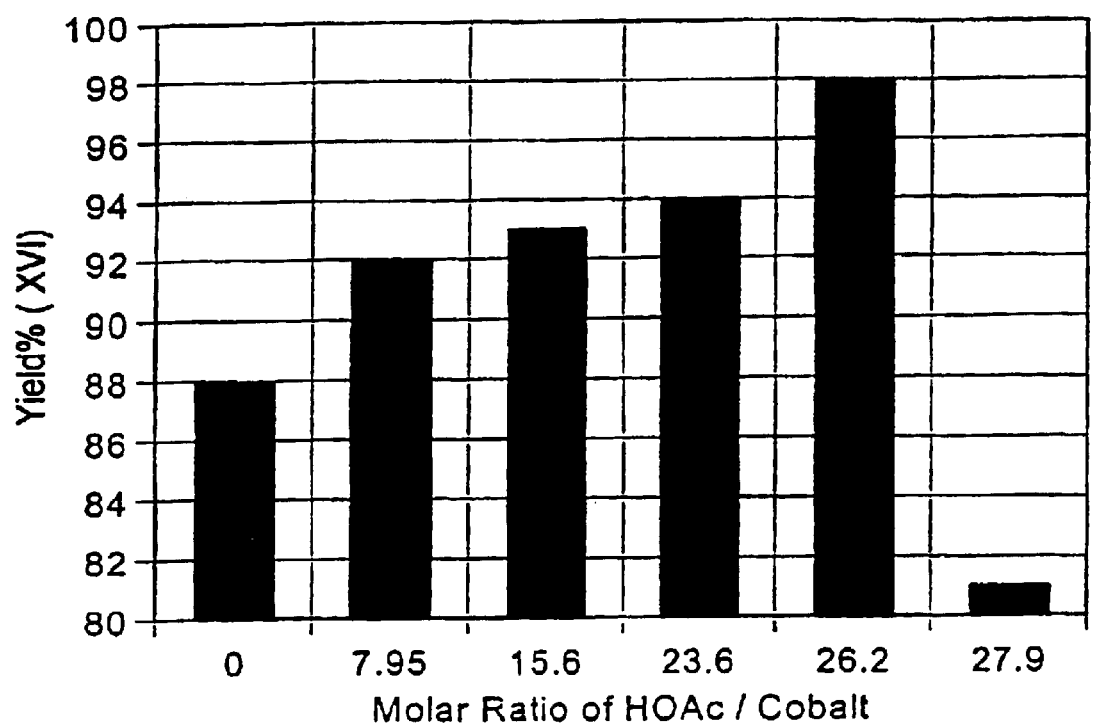
FIG. 1 is a graph of the molar ratio of acetic acid to cobalt versus the yield of N-acetyliminodiacetic acid (XVI) under the conditions described in Example 4.

The process of the present invention is broadly directed to the carboxymethylation of carbamoyl compounds in which strong acid co-catalysts or anhydrous conditions are not required. A preferred embodiment of this process is schematically depicted in Reaction Scheme 1 in which hydridocobalttetracarbonyl is identified for convenience of discussion as the carboxymethylation catalyst precursor:

reaction mixture containing the base pair; aldehyde is then introduced to the reaction mixture to yield the N-acyl amino carboxylic acid reaction product.

A. Preparation of the Base Pair

The base pair is formed by the reaction of a carbamoyl compound and a carboxymethylation catalyst precursor. In general, the carbamoyl compound is an amide, a urea, or a carbamate, preferably an amide or a urea. More preferably, the carbamoyl compound is a compound having the structure (II):

(II)

wherein $R^1$, $R^2$ and $R^{2a}$ are as previously defined.

In one embodiment of the present invention, $R^1$ is hydrocarbyl or substituted hydrocarbyl, typically a $C_1$ to about $C_{20}$ hydrocarbyl or substituted hydrocarbyl. In this embodiment, $R^1$ is preferably $C_1$ to about $C_{10}$, more preferably $C_1$ to about $C_6$, even more preferably $C_1$. In another embodiment of the present invention, $R^1$ is —$NR^3R^4$. In this embodiment, $R^3$ and $R^4$ are independently hydrogen, hydrocarbyl or substi-

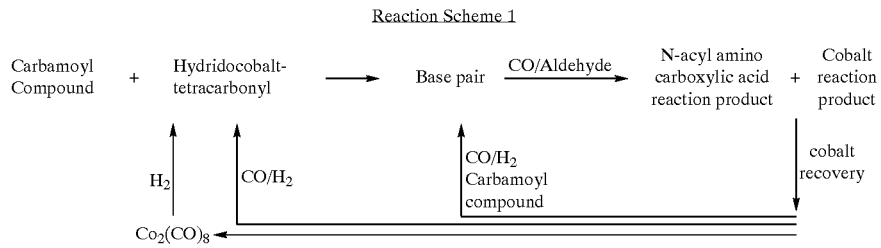

Reaction Scheme 1

As depicted, a carbamoyl compound is reacted with hydridocobalttetracarbonyl to produce a base pair of the present invention. The base pair, when present in a reaction mixture along with carbon monoxide and an aldehyde (or source of aldehyde), reacts to produce an N-acyl amino carboxylic acid reaction product and a cobalt reaction product. The N-acyl amino carboxylic acid reaction product may then be deacylated, for example, by hydrolysis, or otherwise further reacted as described elsewhere herein.

The hydridocobalttetracarbonyl which is reacted to form the base pair, may be obtained in any one of several ways. In one embodiment of the present invention, it is generated in situ in a reaction mixture prepared by combining the carbamoyl compound and dicobaltoctacarbonyl (or other catalyst precursor) in the presence of hydrogen, and optionally carbon monoxide and an aldehyde; as depicted in Reaction Scheme 1, the dicobaltoctacarbonyl may be obtained by recycle and regeneration of a cobalt(II) salt which is recovered from a prior carboxymethylation step. Recovery of a cobalt(II) salt for conversion to cobalt octacarbonyl dimer is described in Weisenfeld, *Ind. Eng. Chem. Res.*, Vol. 31, No. 2, p. 636–638 (1992). In a second embodiment of the present invention, the cobalt(II) salt is regenerated using carbon monoxide and hydrogen by conventional techniques to produce hydridocobalttetracarbonyl which is combined with the carbamoyl compound in a reaction mixture. In a third embodiment of the present invention, the cobalt(II) salt is converted to hydridocobalttetracarbonyl using carbon monoxide and hydrogen in the presence of the carbamoyl compound which produces a tuted hydrocarbyl. In general, if either of $R^3$ and $R^4$ are hydrocarbyl, it is a $C_1$ to about $C_{20}$ hydrocarbyl, preferably $C_1$ to about $C_{10}$, more preferably $C_1$ to about $C_6$, and still more preferably methyl or isopropyl. If $R^3$ or $R^4$ is substituted hydrocarbyl, typically it is $C_1$ to about $C_{20}$ substituted hydrocarbyl, preferably $C_1$ to about $C_{10}$, more preferably $C_1$ to about $C_6$, and still more preferably it is phosphonomethyl (—$CH_2PO_3H_2$), hydroxymethyl (—$CH_2OH$), amidomethyl (—$CH_2N(R')C(O)R''$), carboxymethyl (—$CH_2CO_2H$), or an ester or salt of carboxymethyl or phosphonomethyl. If $R^2$ and $R^{2a}$ are each hydrocarbyl or substituted hydrocarbyl, it is preferred that at least one of $R^3$ and $R^4$ be hydrogen, hydroxymethyl, amidomethyl, or another substituent which, under the carboxymethylation reaction conditions, is capable of producing an N—H bond. In general, preferred amidomethyl substituents correspond to the structure

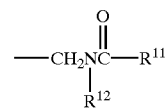

wherein $R^{11}$ and $R^{12}$ are independently hydrogen, hydrocarbyl, substituted hydrocarbyl, hydroxymethyl, carboxymethyl, phosphonomethyl, or an ester or salt of carboxymethyl or phosphonomethyl.

Preferably, at least one of $R^2$ and $R^{2a}$ is hydrogen, hydroxymethyl, or amidomethyl. More preferably, at least one of $R^2$ and $R^{2a}$ is hydrogen. If, however, $R^2$ or $R^{2a}$ is hydrocarbyl, it is typically a $C_1$ to about $C_{20}$ hydrocarbyl, preferably $C_1$ to about $C_{10}$, more preferably $C_1$ to about $C_6$, and still more preferably methyl or isopropyl. If $R^2$ or $R^{2a}$ is substituted hydrocarbyl, typically it is $C_1$ to about $C_{20}$ substituted hydrocarbyl, it is preferably $C_2$ to about $C_{10}$, and more preferably $C_1$ to about $C_6$. The substituted hydrocarbyl can be, for example, phosphonomethyl, hydroxymethyl, amidomethyl, carboxymethyl, an ester or salt of carboxymethyl or phosphonomethyl, or (N'-alkylamido)methyl, preferably phosphonomethyl, carboxymethyl, amidomethyl or an ester or salt of carboxymethyl or phosphonomethyl. It is possible for $R^2$ and $R^{2a}$ to be non-identical. For example, $R^2$ can be hydrocarbyl and $R^{2a}$ can be substituted hydrocarbyl. In one embodiment, $R^2$ can be an alkyl such as methyl while $R^{2a}$ can be, for example, an (N'-alkylamido)methyl group such as (N'-methylamido)methyl or hydroxymethyl.

The carboxymethylation catalyst precursor which is reacted with the carbamoyl compound to form the base pair may be any composition which is known to be useful in carboxymethylation reactions which generally contain a metal from Group VIII of the Periodic Table (CAS version). These compositions are referred to as carboxymethylation catalyst precursors herein since the precise form of the catalyst participating in the reaction has not been determined with certainty. Without being bound to any particular theory, however, it is presently believed that the base pair itself, which is produced by the interaction of the carboxymethylation catalyst precursor and the carbamoyl compound in the presence of carbon monoxide and hydrogen, serves as the catalyst for the carboxymethylation reaction. In any event, the carboxymethylation catalyst precursor is preferably derived from cobalt or palladium, preferably cobalt, and still more preferably the carboxymethylation catalyst precursor is derived from cobalt metal, cobalt oxide, organic and inorganic salts, for example, halides such as cobalt chloride and cobalt bromide, aromatic and aliphatic carboxylates such as cobalt acetate, cobalt propionate, cobalt octanoate, cobalt stearate, cobalt benzoate and cobalt naphthenate, and complex compounds containing one or more ligands such as carbonyls, nitriles and phosphines. The preferred cobalt containing carboxymethylation catalyst precursors are dicobalt octacarbonyl ($Co_2(CO)_8$), hydridocobalttetracarbonyl ($HCo(CO)_4$), cobalt tetracarbonyl anion ($[Co(CO)_4]^1$) or a cobalt(II) salt.

Depending upon the nature of the carbamoyl compound, the base pair may be formed in the presence of the aldehyde (or an aldehyde source which may contain water) and carbon monoxide or it is first formed and then combined with the aldehyde source. When the carbamoyl compound is an amide such as acetamide, the reaction mixture may be formed by introducing the amide, aldehyde source, carbon monoxide, and carboxymethylation catalyst precursor to the mixture without premixing the amide and the carboxymethylation catalyst precursor to form the base pair; as a result, the base pair is formed in the presence of the aldehyde source. To obtain significant yields of N-acyl amino carboxylic acid reaction product when urea or a substituted urea such as bis-phosphonomethylurea is used as the carbamoyl compound, however, the base pair is preferably formed in the essential absence of water and aldehyde sources which contain water; under these conditions, the base pair is obtained in good yield. The resulting base pair is then mixed with the aldehyde source and carbon monoxide.

Without being bound to any particular theory and based upon experimental evidence obtained to date, it appears that the formation of the desired base pair is related to the basicity of the carbamoyl compound; that is, carbamoyl compounds such as acetamide appear to be sufficiently basic to produce the desired base pair in the presence of water and aldehyde sources which contain water whereas ureas which are less basic than acetamide do not. Stated another way, experimental evidence obtained to date suggests (1) the carboxymethylation catalyst precursor deprotonates under the carboxymethylation reaction conditions and forms a base pair with various species in the reaction mixture, (2) only those base pairs formed with the carbamoyl compound are productive (that is, will lead to the formation of the N-acyl amino carboxylic acid reaction product), and (3) amides such as acetamide will sufficiently base pair with hydridocobalttetracarbonyl anion in the presence of an aldehyde source which contains water whereas urea and comparable bases will not.

B. Carboxymethylation Reaction

In the process of the present invention, the base pair which is formed is reacted with carbon monoxide and an aldehyde (or an aldehyde source) in a carboxymethylation reaction to produce an N-acyl amino carboxylic acid reaction product.

The pressure at which the carboxymethylation reaction is carried out may be from about 200 psi to about 4000 psi (about 1,400 kPa to about 28,000 kPa). Preferably, the pressure is from about 1000 to about 3700 psi (about 7,000 kPa to about 26,000 kPa), and more preferably from about 1250 to about 3500 psi (about 9,000 kPa to about 24,000 kPa).

In the carboxymethylation reaction, hydrogen or other diluent gases, such as nitrogen or helium may be introduced with the carbon monoxide. Preferably, the atmosphere contains a significant partial pressure of hydrogen. Typically, the partial pressure ratio of carbon monoxide to hydrogen will be at least about 1:1, preferably about 70:30 to about 99:1, and more preferably from about 85:15 to about 97:3.

In general, the carboxymethylation reaction can be run at any temperature at which the reactants and equipment can be conveniently handled. Typically, the reaction temperature will be within the range of about 50° C. to about 170° C., preferably is about 65° C. to about 140° C., more preferably is about 80° C. to about 130° C., and still more preferably is about 95° C. to about 115° C.

The mole ratio of carbamoyl compound to carboxymethylation catalyst metal atoms can vary over the range of about 0.1 to about 30. Preferably, it is about 0.5 to about 15, more preferably about 2 to about 13.

Aldehydes useful in the process of the present invention may be present in pure form, in a polymeric form, in an aqueous solution, or as an acetal. A broad range of aldehydes can be used; the aldehyde may contain more than one formyl group and, in addition to the oxygen atom(s) of the formyl group(s), the aldehyde may contain other oxygen atoms or other heteroatoms, such as in furfurylacetaldehyde, 4-acetoxyphenylacetaldehyde, and 3-methylthiopropionaldehyde. More suitably, the aldehyde is of the general formula R—CHO wherein R is hydrogen, hydrocarbyl, or substituted hydrocarbyl. In general, R contains up to 20 carbon atoms, more suitably up to 10 carbon atoms. Examples of such aldehydes are phenylacetaldehyde, formylcyclohexane, and 4-methylbenzaldehyde. Preferably, R is hydrogen, a linear or branched alkyl group containing up to 6 carbon atoms, or an arylalkyl group where the aryl contains 6 to 12 carbon atoms and the alkyl contains up to 6 carbon atoms. More preferably, the aldehyde is formaldehyde, acetaldehyde, 3-methylthiopropionaldehyde or isobutyraldehyde, and in a particularly preferred embodiment, the aldehyde is formaldehyde with the source of the formaldehyde being formalin.

In one embodiment of the present invention, an acid co-catalyst is included in the reaction mixture. For some carbamoyl compounds, such as acetamide (and acetamide equivalents), the acid co-catalyst is preferably an organic acid, such as a carboxylic acid, having a $pK_a$ greater than about 3. The organic acid co-catalyst can be, for example, formic acid, acetic acid, or propionic acid, preferably formic acid or acetic acid, and most preferably acetic acid. In general, when the carbamoyl compound is an amide, it is preferred that the organic acid co-catalyst be the carboxylic acid which corresponds to the amide (i.e., the carboxylic acid of which the amide is a derivative).

The carboxymethylation reaction can be run in the presence of a solvent which is chemically and physically compatible with the reaction mixture. Preferably, the solvent is a weaker base than the carbamoyl compound. The solvent can be, for example, an ether, a ketone, an ester, a nitrile, a carboxylic acid, a formamide such as dimethylformamide, or a mixture thereof. Preferably, the solvent is an ether, a ketone, or a nitrile; more preferably, the solvent can be ethylene glycol, dimethoxyethane (DME), tetrahydrofuran (THF), acetone, 2-butanone, acetonitrile, acetic acid, or t-butyl methyl ether.

In a preferred embodiment, the carboxymethylation reaction is carried out in the presence of water. In this embodiment, the molar ratio of water to the carbamoyl compound in the carboxymethylation reaction mixture is generally less than about 10:1, preferably between about 2:1 and about 5:1, and more preferably between about 3:1 and about 4:1.

Payload is measured as the mass of carbamoyl compound divided by the mass of reaction solvent. One skilled in the art will recognize that useful ranges of payload will depend in part on the physical state of the carbamoyl compound starting material under the reaction conditions employed and its compatibility with solvents used. The payload typically will vary through the range of about 0.001 grams of carbamoyl compound per gram of solvent ($g_c/g_s$) in the reaction mixture to about 1 $g_c/g_s$. Preferably, it is at least about 0.01 $g_c/g_s$, more preferably at least about 0.1 $g_c/g_s$, still more preferably between about 0.12 $g_c/g_s$ and about 0.35 $g_c/g_s$, and in a particularly preferred embodiment, between about 0.15 $g_c/g_s$ and about 0.3 $g_c/g_s$.

The reaction can be carried out in a batch mode or in a continuous mode. When run in a continuous mode, the residence time in the reaction zone can vary widely depending on the specific reactants and conditions employed. Typically, residence time can vary over the range of about 1 minute to about 500 minutes, preferably about 10 minutes to about 250 minutes, more preferably about 30 minutes to about 100 minutes. When run in a batch mode, reaction time typically varies over the range of about 10 seconds to about 12 hours, preferably about 2 minutes to about 6 hours, more preferably about 10 minutes to about 3 hours.

C. Carboxymethylation Catalyst Recovery

After the carboxymethylation reaction, the catalyst is preferably recovered for reuse in a subsequent carboxymethylation reaction. The nature of the recovery step will vary depending on the catalyst and any recovery method of the catalyst which is compatible with the carboxymethylation reaction mixture and products can be used.

Weisenfeld (U.S. Pat. No. 4,954,466) reported a method of recovering cobalt catalyst values from carboxymethylation reaction mixtures wherein a cobalt-N-acetyliminodiacetic acid complex was dissolved in an aqueous solution with a strong acid and then extracted with a hydrocarbon solvent containing a trialkylamine to transfer the cobalt from the aqueous solution into the hydrocarbon solvent. The cobalt was then stripped from the hydrocarbon solvent with water and precipitated with a strong base.

Another method for the recovery of cobalt catalyst values from carboxymethylation reaction mixtures is described in European Patent Application Publication No. EP 0 779 102 A1. In that method, cobalt is recovered from carboxymethylation reaction mixtures such as those yielding N-acylsarcosines by treatment of the finished reaction mixture with aqueous hydrogen peroxide or aqueous hydrogen peroxide and sulfuric acid, thereby converting the cobalt catalyst to water-soluble cobalt(II) salts. The aqueous phase containing the water-soluble cobalt(II) salts is then separated from the non-aqueous phase. Excess hydrogen peroxide is next removed from the aqueous phase, for example, by heating. An alkali metal hydroxide is then added to the aqueous phase causing the precipitation of cobalt(II) hydroxide. The cobalt(II) hydroxide is then collected and washed in preparation for regeneration to cobalt catalyst.

Alternatively, and in accordance with one aspect of the present invention, cobalt from a completed carboxymethylation reaction mass is oxidized to a soluble cobalt (II) species. The oxidation step is carried out by exposing the carboxymethylation reaction mixture upon completion to a molecular oxygen-containing gas for a suitable length of time. The exposure to oxygen can be achieved by any convenient means, for example, by bubbling the oxygen-containing gas through the reaction mixture or by maintaining an atmosphere of the oxygen-containing gas over the reaction mixture. The progress of the reaction can be monitored by color changes in which the final oxidized system is a deep red or red-purple color which undergoes no further changes. Alternatively, the progress of the reaction can be monitored by infrared spectroscopy or by cyclic voltametry.

The concentration of molecular oxygen in the oxygen-containing gas used in the cobalt recovery step of the present invention can vary depending on the reaction conditions. The concentration of oxygen is typically about 0.1% by weight to 100% by weight. Greater concentrations of oxygen in the oxygen-containing gas will typically cause faster oxidation reaction rates. However, relatively low concentrations of oxygen in the oxygen-containing gas are favored when volatile organic solvents are present in the reaction mixture, thereby presenting a safety risk. Preferably, the concentration of oxygen in the oxygen-containing gas is from about 5 wt. % to about 80 wt. %, more preferably from about 10 wt. % to about 30 wt. %. The oxygen-containing gas can also contain a diluent gas. Preferably the diluent is inert under the reaction conditions. Typical diluent gases are nitrogen, helium, neon, and argon, preferably nitrogen. Air can conveniently be used as the oxygen-containing gas. The oxidation can be carried out under subatmospheric pressure, atmospheric pressure, or superatmospheric pressure. Preferably it is carried out at pressures ranging from about 10 psi to about 100 psi (about 70 to about 700 kPa), more preferably about 30 to about 60 psi (about 200 to about 400 kPa).

The oxidized cobalt(II) species may be converted in situ into an insoluble cobalt (II) salt complex with the N-acyl amino carboxylic acid reaction product by allowing the reaction mixture to stand for a suitable length of time. For example, it is convenient to allow the reaction mixture to stand overnight to achieve the precipitation of the insoluble cobalt(II) salt complex. As the insoluble cobalt(II) salt complex forms, it precipitates out of solution.

Formation and precipitation of the insoluble cobalt(II) salt complex can be accelerated by raising the temperature of the system. The temperature of the reaction mixture during the oxidation step and during the complex-formation step of the present invention typically ranges from about room temperature to about 150° C., preferably from about 60° C. to about 110° C., more preferably from about 70° C. to about 100° C.

Alternatively, the formation and precipitation of the oxidized cobalt(II) salts is facilitated by the presence of a composition such as an organic acid (for example, formic, acetic, oxalic, or propionic) which is present in the carboxymethylation step. Alternatively, the composition may be introduced upon completion of the carboxymethylation reaction step. The insoluble cobalt(II) salt complex can be separated from the reaction mass by any convenient means, for example, by filtration or centrifugation, and subsequently recycled to fresh cobalt catalyst for use in additional carboxymethylation reaction. The oxidation to the cobalt(II) species and conversion of the cobalt(II) species to an insoluble cobalt(II) salt complex can optionally be performed as two discrete steps or combined into a single step in which oxidation and salt formation are carried out in a nearly simultaneous fashion.

As a further alternative, the formation and precipitation of the oxidized cobalt(II) salts may also be accelerated by the addition of a solvent. Typical solvents include dimethylether ("DME"), acetone, or any solvent suitable in the carboxymethylation step. In general, the amount of excess solvent is at least 50% of the volume of the reaction mass, more preferably about 75% to about 150% of the reaction mass, and most preferably between about 90% and about 110% of the reaction mass.

Instead of introducing molecular oxygen to the carboxymethylation reaction mixture, the cobalt (II) species may be formed under anaerobic conditions. In this approach, the reaction mixture is simply heated, refluxed or distilled at a temperature of about 60° C. to about 100° C. to effect the precipitation of an insoluble cobalt(II) salt. See, for instance, Example 27. In addition, the formation and precipitation of the oxidized cobalt(II) salts may also be accelerated by the presence of an organic acid or by the addition of a solvent as previously described in the case when molecular oxygen is introduced to the system.

D. Catalyst Regeneration

Several methods for regenerating a cobalt catalyst have been reported in the literature which may be used in accordance with one aspect of the present invention. For example, in U.S. Pat. No. 4,954,466 Weisenfeld suggests converting a cobalt (II) precipitate to dicobaltoctacarbonyl by reacting the precipitate with carbon monoxide and hydrogen at a temperature of 150 to 180° C. with a pressure of 1500 to 6000 psig (10,345 to 41,380 kPa).

Another method for regenerating a carboxymethylation cobalt catalyst is described in European Patent Application Publication No. EP 0 779 102 A1. In that method, cobalt hydroxide recovered from a carboxymethylation reaction is introduced into the melt of an N-acyl amino acid derivative such as an N-acylsarcosine. The mixture is then added to a polar aprotic solvent and reacted with carbon monoxide or a mixture of carbon monoxide and hydrogen to form a carboxymethylation catalytic mixture.

Surprisingly, it has been discovered that the rate of regeneration of the cobalt(II) salt can be dramatically increased if it is reacted with a carbamoyl compound of the present invention along with carbon monoxide and hydrogen. Advantageously, the product of this reaction is the base pair which participates in the carboxymethylation step. When the carbamoyl compound is an amide, therefore, productivity is significantly increased by regenerating the cobalt (II) salt in the presence of the amide. In addition, when the carbamoyl compound is a urea, the resulting base pair will react with carbon monoxide and an aldehyde to produce an N-acyl amino carboxylic acid reaction product in relatively good yield; a product which is not believed to have been previously reported to have been obtained by a carboxymethylation reaction.

In accordance with the present invention, therefore, when the carbamoyl compound is an amide the cobalt(II) salt can be regenerated in the presence of the amide, an aldehyde, the amide and the aldehyde, or neither the amide or the aldehyde. When the carbamoyl compound is urea (or other compound which is a less competent base than the amides), however, the cobalt(II) salt is preferably regenerated in the presence of the carbamoyl compound and in the essential absence of water and aldehyde sources which contain water. If the active catalyst mixture is regenerated in the absence of the carbamoyl compound, therefore, it is further advantageous to add the carbamoyl compound to the reaction mixture before the addition of the aldehyde source. For example, when the carbamoyl compound is a urea (structure (II) wherein R' is $—NR^3R^4$), it is advantageous to treat the cobalt(II) salt with carbon monoxide, hydrogen, and urea before the aldehyde source is added to the reaction mixture.

During regeneration, the reaction pressure generally ranges from about 200 psi to about 4,000 psi (1,400 to about 28,000 kPa), preferably from about 800 psi to about 3,700 psi (5,600 to about 26,000 kPa), and more preferably from about 1,500 psi to about 3,500 psi (10,500 to about 24,000 kPa). In general, the carbon monoxide-to-hydrogen partial pressure ratio during regeneration ranges from about 99:1 to about 1:99, preferably from about 30:70 to about 90:10, and more preferably from about 50:50 to about 75:25. The progress of the regeneration reaction can be followed by monitoring the uptake of gas, for example, by monitoring head pressure. During the regeneration step it is often advantageous to heat the reaction mixture. Typically, reaction mixture temperatures range from about 70° C. to about 170° C., preferably from about 90° C. to about 150° C., and more preferably from about 100° C. to about 140° C. Reaction times for the regeneration step can vary from about 1 minute to about 5 hours, preferably from about 5 minutes to about 2 hours, and more preferably from about 10 minutes to about 1 hour. If desired, the regeneration step can be performed in the presence of the organic acid co-catalyst used in the carboxymethylation step. The regenerated active catalyst complex can, if desired, be used in a carboxymethylation reaction directly after regeneration.

The anionic portion of the cobalt(II) salt is not critical to the regeneration step. For example, the cobalt(II) can be in the form of a salt of the conjugate base of the carboxymethylation reaction product from which the cobalt(II) was recovered. Alternatively, the cobalt(II) can be in any other convenient form such as cobalt acetate tetrahydrate, cobalt stearate, cobalt acetonate, or cobalt oxalate.

E. Deacylation

In many embodiments of the present invention, it is desired to deacylate the N-acyl amino carboxylic acid reaction product which results from the carboxymethylation step. In general, deacylation can be achieved by hydrolysis or by the formation of a diketopiperazine species.

In general, the N-acyl amino carboxylic acid reaction product is hydrolyzed in the presence of a hydrolysis catalyst, for example an acid or a base, preferably a mineral acid. Suitable mineral acids useful for this purpose include hydrochloric acid, sulfuric acid, nitric acid, phosphoric acid, or phosphorous acid. Alternatively, the N-acyl reaction product may be hydrolyzed in the absence of a mineral acid to form an amino acid by heating the N-acyl amino carboxylic acid reaction product in the presence of water.

Instead of being hydrolyzed, the N-acyl amino carboxylic acid reaction product can be deacylated and cyclized in a single step to form 2,5-diketopiperazines as depicted in Reaction Scheme 2:

Reaction Scheme 2

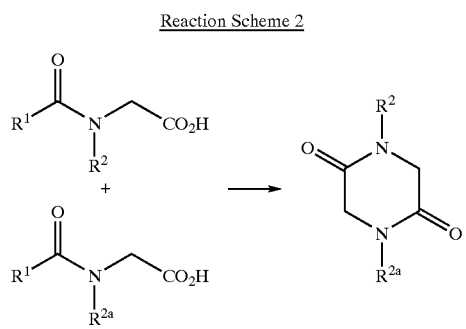

wherein $R^2$ and $R^{2a}$ are independently hydrogen, alkyl, or carboxymethyl or the salts or esters thereof. Examples of such reactions include the preparation of 1,4-di(carboxymethyl)-2,5-diketopiperazine (XVII) from N-acetyliminodiacetic acid (XVI) (see Reaction Scheme 7), the preparation of 2,5-diketopiperazine (XXX) from N-acetylglycine (XVIII) (see Reaction Scheme 9a), and the preparation of 1,4-dimethyl-2,5-diketopiperazine (XXXI) from N-acetyl-N-methylglycine (XX) (See Reaction Schemes 11 and 15).

Typically, reaction temperatures for formation of the diketopiperazines ranges from about 100° C. to about 250° C., preferably about 150° C. to about 220° C., more preferably about 185° C. to about 200° C. The reaction is relatively rapid, and reaction time typically ranges from about 1 minute to about 10 hours, preferably about 5 minutes to about 5 hours, still more preferably about 10 minutes to about 3 hours. The amount of added water measured as a percent of the starting material generally ranges up to about 85 wt. %, preferably from about 5 wt. % to about 70 wt. %, and more preferably from about 9 wt. % to about 20 wt. %. If desired, a catalyst can be added to the reaction mixture. Preferably, it is an organic acid and still more preferably it is a $C_1$ to about $C_3$ carboxylic acid. Most preferably, the acid catalyst is acetic acid. Solvents can optionally be present in the reaction mixture. For example, ethers, ketones, or nitriles can be added.

The formation of the 2,5-diketopiperazines from N-acyl amino acid reaction products is advantageous for a number of reasons. As a general rule, they are less soluble in many solvents and in water than is the corresponding amino acid. As a result, the diketopiperazine can be more readily precipitated from the reaction mixture, separated, and handled. Furthermore, since the deacylation reaction does not require strong mineral acids, it is less corrosive to process equipment than a hydrolysis reaction in which strong mineral acids are employed.

The deacylation and hydrolysis reactions of N-acyl amino acid reaction products can occur simultaneously, resulting in a mixture of products. This mixture of deacylation and hydrolysis products can be subsequently used as produced, i.e., without separation and purification, or it can be separated into its component products.

The ratio of hydrolysis and deacylation products achieved in the final reaction mixture depends on the conditions selected for the reaction. For example, in Reaction Scheme 3, N-acetyliminodiacetic acid (XVI) is heated in water to form iminodiacetic acid (XIV), 1,4-di(carboxymethyl)-2,5-diketopiperazine (XVII) or mixtures thereof.

Reaction Scheme 3

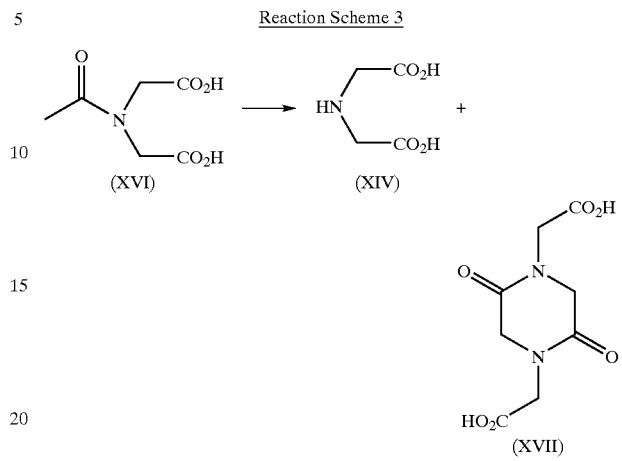

The ratio of (XIV) to (XVII) can be controlled as a function of the various conditions under which the reaction is performed. For example, Table 1 demonstrates the effect upon the ratio of (XIV) to (XVII) as a consequence of heating N-acetyliminodiacetic acid (XVI) (45 grams) under varying conditions of temperature, time, added water, and added acetic acid. (See Example 28 for a more complete description).

TABLE 1

| Ex. No. | Temperature (° C.) | Time (min) | Added water (g) | Added Acetic Acid (g) | Yield of (XVII) (g) | Yield of (XIV) (g) | Ratio of (XVII) to (XIV) |
|---|---|---|---|---|---|---|---|
| 28.1 | 175 | 90 | 0 | 10 | 22.98 | 0.85 | 27.0 |
| 28.2 | 175 | 20 | 0 | 10 | 19.26 | 1.76 | 10.9 |
| 28.3 | 175 | 45 | 0 | 0 | 23.71 | 0.69 | 34.4 |
| 28.4 | 175 | 20 | 5 | 10 | 18.66 | 3.37 | 5.5 |
| 28.5 | 195 | 45 | 0 | 10 | 23.98 | 0.36 | 66.6 |
| 28.6 | 195 | 45 | 5 | 0 | 24.78 | 0.29 | 85.4 |
| 28.7 | 195 | 45 | 5 | 10 | 23.74 | 0.83 | 28.6 |
| 28.8 | 195 | 20 | 5 | 10 | 23.15 | 0.92 | 25.2 |
| 28.9 | 195 | 5 | 5 | 10 | 21.29 | 1.23 | 17.3 |

Reaction conditions can be selected, if desired, which maximize the amount of compound (XVII) formed relative to the amount of compound (XIV) formed. By way of illustration, Examples 28.1 and 28.2 and Examples 28.7, 28.8 and 28.9 show that longer reaction times tend to increase the ratio of (XVII) to (XIV). Similarly, Examples 28.4 and 28.8 demonstrate that higher temperatures tend to increase the ratio of (XVII) to (XIV). In contrast, Examples 28.2 and 28.4 show that increasing the amount of added water decreases the ratio of (XVII) to (XIV). Examples 28.6 and 28.7 show that increasing the amount of added carboxylic acid, in this case, acetic acid, decreases the ratio of (XVII) to (XIV). At temperatures less than 100° C., the reaction can require several hours. By increasing pressure on the reaction system, temperatures well in excess of 100° C. can be achieved and under these conditions hydrolysis and deacylation can be achieved in much shorter periods of time, for example in minutes.

In general, a wide variety of N-acyl amino carboxylic acid reaction products useful in the present invention can be hydrolyzed or deacylated using the conditions described herein. Examples of N-acyl amino carboxylic acid reaction products which can be hydrolyzed or deacylated and the products of the reactions as described herein are set forth in Table 2.

TABLE 2

Examples of hydrolysis or deacylation products

| N-acyl amino carboxylic acid reaction product Starting Material | Hydrolysis Product | Deacylation Product |
|---|---|---|
| N,N,N',N'-tetra(carboxymethyl) urea (XIII) | Iminodiacetic acid (XIV) | None |
| N-acetyl-iminodiacetic acid (XVI) | Iminodiacetic acid (XIV) | 1,4-di(carboxymethyl)-2,5-diketopiperazine (XVII) |
| N-acetyl-N-(phosphonomethyl) glycine (XIX) | N-(phosphonomethyl) glycine (I) | 1,4-di(phosphonomethyl)-2,5-diketopiperazine |
| N,N'-di(carboxymethyl)-N,N'-dimethyl urea (XXII) | Sarcosine (XXIII) | None |
| N,N'-di(carboxymethyl)-N,N'-di(phosphonomethyl) urea (XXIV) | N-(phosphonomethyl) glycine (I) | None |
| N-acetyl-N-methyl glycine | N-methylglycine (XX) | 1,4-dimethyl-2,5-diketopiperazine (XXXI) |
| N-acetylglycine (XVIII) | Glycine | 2,5-diketopiperazine (XXX) |

F. Phosphonomethylation

In certain embodiments of the present invention it is preferred that the N-acyl reaction product be phosphonomethylated. Phosphonomethylation reactions of amines and of amino acids have been reported. For example, Moedritzer, et al. (J. Org. Chem. 1966, 31, 1603–1607) reported the reaction of primary and secondary amino acids with phosphorous acid and formaldehyde to form, respectively, di- and mono-phosphonomethylated amino acids. Moedritzer also reported (U.S. Pat. No. 3,288,846) the reaction of iminodiacetic acid (XIV) with phosphorous acid and formaldehyde to prepare N-(phosphonomethyl)-iminodiacetic acid (XV). Miller et al. (U.S. Pat. No. 4,657,705) disclose a process in which substituted ureas, amides and carbamates are phosphonomethylated to produce an N-substituted aminomethylphosphonic acid which can be converted to glyphosate; in the disclosed process, the urea, amide or carbamate is (1) mixed with an aqueous acidic medium comprising phosphorous acid and an acid selected from among sulfuric, hydrochloric and hydrobromic acids and (2) heated to a temperature between about 70 and about 120° C. Phosphonomethylation reactions can also be carried out using phosphorous trichloride instead of phosphorous acid (for example, U.S. Pat. No. 4,400,330).

Typically, the N-acyl amino carboxylic acid reaction product to be phosphonomethylated is treated with a source of phosphorous acid and a source of formaldehyde. Another mineral acid such as sulfuric acid or hydrochloric acid is preferably added. Reaction temperatures generally range from about 80° C. to about 150° C., preferably from about 100° C. to about 140° C., more preferably from about 120° C. to about 140° C. Reaction times generally range from about 10 minutes to about 5 hours, preferably from about 20 minutes to about 3 hours, more preferably from about 30 minutes to about 2 hours. Any source of phosphorous acid or phosphorous acid equivalent can be used in the phosphonomethylation reaction. For example, phosphorous acid, phosphorous trichloride, phosphorous tribromide, phosphorous acid esters, chlorophosphonic acid and esters of chlorophosphonic acid can be used. Phosphorous acid and phosphorous trichloride are preferred. Formaldehyde can be derived from any source, for example, paraformaldehyde or formalin.

In one embodiment of the present invention, the phosphonomethylation reaction results in the replacement of the N-acyl substituent of the N-acyl amino carboxylic acid reaction product with an N-phosphonomethyl group to produce an N-(phosphonomethyl)amino acid. This reaction is shown generically in Scheme 4 wherein $R^1$ and $R^2$ are as defined previously.

Reaction Scheme 4

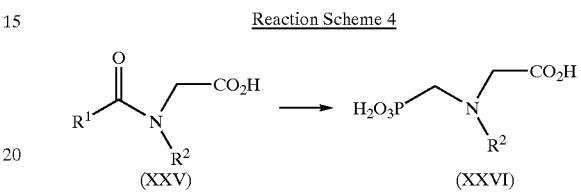

Examples of this type of reaction include the conversion of N-acyl sarcosine to N-methyl-N-(phosphonomethyl) glycine, N-acyliminodiacetic acid to N-(phosphonomethyl) iminodiacetic acid, and N-acylglycine to glyphosate.

In another embodiment of the present invention, 2,5-diketopiperazines are phosphonomethylated with phosphorous trichloride, phosphorous acid, or a source of phosphorous acid in the presence of a source of formaldehyde to form N-substituted-N-(phosphonomethyl)glycine as shown in Reaction Scheme 4a.

Reaction Scheme 4a

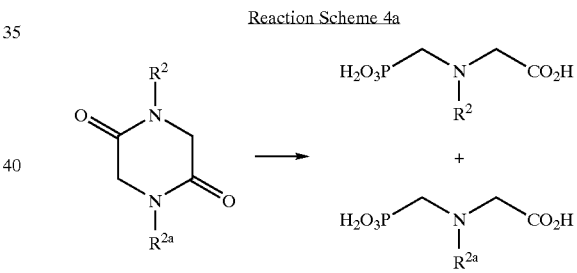

wherein $R^2$ and $R^{2a}$ are independently hydrogen, alkyl, or carboxymethyl or the salts or esters thereof.

In a further embodiment of the present invention, an N-acylglycine is phosphonomethylated to form N-(phosphonomethyl)glycine (I). For example, the reaction of N-acetylglycine (XVIII), phosphorous acid or phosphorous trichloride, and a source of formaldehyde produces N-(phosphonomethyl)glycine (I) (See Reaction Scheme 9).

In still further aspect of the present invention, N-acyl-N-alkylglycine compounds can be phosphonomethylated to produce N-alkyl-N-(phosphonomethyl)glycine compounds. For example, N-acetyl-N-methylglycine (XX) can be reacted with a source of formaldehyde and with phosphorous acid or phosphorous trichloride to produce N-methyl-N-(phosphonomethyl)glycine (XXI) (See Reaction Schemes 12 and 16).

G. Oxidative Dealkylation

In one embodiment of the present invention, the carboxymethylation reaction product is converted to N-alkyl-N-(phosphonomethyl) glycine ("N-substituted glyphosate") which is oxidatively dealkylated to generate N-(phosphonomethyl)glycine. Preferably, oxidation is carried out by combining the N-substituted glyphosate with water and feeding the combination into a reactor along with an oxygen-containing gas or a liquid containing dissolved oxygen. In the presence of a noble metal catalyst, the N-substituted glyphosate reactant is oxidatively converted into glyphosate and various byproducts:

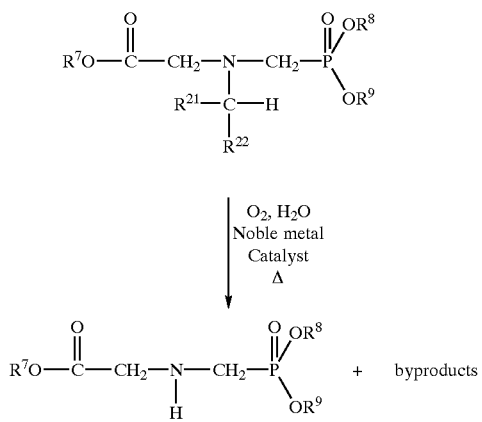

wherein $R^7$, $R^8$, and $R^9$ are as previously defined, and $R^{21}$ and $R^{22}$ are independently hydrogen, halogen, $-PO_3H_2$, $-SO_3H_2$, $-NO_2$, hydrocarbyl or unsubstituted hydrocarbyl other than $-CO_2H$.

In a preferred embodiment, the catalyst subsequently is separated by filtration and the glyphosate then is isolated by precipitation, for example, by evaporation of a portion of the water and cooling.

The amount of N-substituted glyphosate reactant in the aqueous medium is typically from about 1 to about 80 wt. % ([mass of N-substituted glyphosate reactant÷total reaction mass]×100%). More preferably, the amount of N-substituted glyphosate reactant is from about 5 to about 50 wt. %, and most preferably from about 20 to about 40 wt. %.

Preferably, the reaction is conducted at a temperature of from about 50° C. to about 200° C. More preferably, the reaction is conducted at a temperature of from about 70° C. to about 150° C., and most preferably from about 125° C. to about 150° C.

The pressure in the reactor during the oxidation generally depends on the temperature used. Preferably, the pressure is sufficient to prevent the reaction mixture from boiling. If an oxygen-containing gas is used as the oxygen source, the pressure also preferably is adequate to cause the oxygen to dissolve into the reaction mixture at a rate sufficient to sustain the desired rate of reaction. The pressure preferably is at least equal to atmospheric pressure. Preferably, the pressure is from about 30 to 200 psig. More preferably, when the temperature is in the most preferred range of from about 125 to about 150° C., the pressure is from about 40 to about 100 psig.

The oxygen source for the oxidation reaction may be any oxygen-containing gas or a liquid containing dissolved oxygen. Preferably, the oxygen source is an oxygen-containing gas. As used herein, an "oxygen-containing gas" is any gaseous mixture containing molecular oxygen which optionally may contain one or more diluents which are non-reactive with the oxygen or the reactant or product under the reaction conditions. Examples of such gases are air, pure molecular oxygen, or molecular oxygen diluted with helium, argon, neon, nitrogen, or other non-molecular oxygen-containing gases. Preferably, at least about 20% by volume of the oxygen-containing gas is molecular oxygen, and more preferably, at least about 50% of the oxygen-containing gas is molecular oxygen.

The oxygen may be introduced by any conventional means into the reaction medium in a manner which maintains the dissolved oxygen concentration in the reaction mixture at the desired level. If an oxygen-containing gas is used, it preferably is introduced into the reaction medium in a manner which maximizes the gas' contact with the reaction solution. Such contact may be obtained, for example, by dispersing the gas through a diffuser such as a porous glass frit or by sintering, shaking, or other methods known to those skilled in the art.

The oxygen preferably is fed to the reaction mixture at a rate which is sufficient to maintain the dissolved oxygen concentration at a finite level. More preferably, the oxygen is fed at a rate sufficient to maintain the dissolved oxygen concentration at a value of no more than about 2 ppm, while sustaining the desired reaction rate. It should be noted that the partial pressure of the oxygen in the reactor affects the rate at which oxygen is delivered to the reaction mixture and preferably is from about 0.5 to about 10 atm.

The catalyst comprises a noble metal, preferably platinum (Pt), palladium (Pd), rhodium (Rh), iridium (Ir), osmium (Os), or gold (Au). In general, platinum and palladium are more preferred, and platinum is most preferred. Because platinum is presently most preferred, much of the following discussion will be directed to use of platinum. It should be understood, however, that the same discussion is generally applicable to the other noble metals and combinations thereof.

The noble metal catalyst may be unsupported, e.g., platinum black, commercially available from various sources such as Aldrich Chemical Co., Inc., Milwaukee, Wis.; Engelhard Corp, Iselin, N.J.; and Degussa Corp., Ridgefield Park, N.J. Alternatively, the noble metal catalyst may be deposited onto the surface of a support, such as carbon, alumina ($Al_2O_3$), silica ($SiO_2$), titania ($TiO_2$), zirconia ($ZrO_2$), siloxane, or barium sulfate ($BaSO_4$), preferably silica, titania, or barium sulfate. Supported metals are common in the art and may be commercially obtained from various sources, e.g., 5% platinum on activated carbon, Aldrich Catalogue No. 20,593-1; platinum on alumina powder, Aldrich Catalogue No. 31,132-4; palladium on barium sulfate (reduced), Aldrich Catalogue No. 27,799-1; and 5% Palladium on activated carbon, Aldrich Catalogue No. 20,568-0. As to carbon supports, graphitic supports generally are preferred because such supports tend to have greater glyphosate selectivity.

The concentration of the noble metal catalyst on a support's surface may vary within wide limits. Preferably it is in the range of from about 0.5 to about 20 wt. % ([mass of noble metal÷total mass of catalyst]×100%), more preferably from about 2.5 to about 10 wt. %, and most preferably from about 3 to about 7.5 wt. %. At concentrations greater than about 20 wt. %, layers and clumps of noble metal tend to form. Thus, there are fewer surface noble metal atoms per total amount of noble metal used. This tends to reduce the catalyst's activity and is an uneconomical use of the costly noble metal.

The weight ratio of the noble metal to the N-substituted glyphosate reactant in the reaction mixture preferably is from about 1:500 to about 1:5. More preferably, the ratio is from about 1:200 to about 1:10, and most preferably from about 1:50 to about 1:10.

In a preferred embodiment, a molecular electroactive molecule (i.e., a molecular species that may be reversibly oxidized or reduced by electron transfer) is adsorbed to the noble metal catalyst. It has been discovered in accordance with this invention that selectivity and/or conversion of the noble metal catalyst may be improved by the presence of the electroactive molecular species, particularly where the catalyst is being used to effect the oxidation of NMG to form glyphosate. In this instance, the electroactive adsorbate preferably is hydrophobic and has an oxidation potential ($E_{1/2}$) of at least about 0.3 volts vs. SCE (saturated calomel electrode). A compilation of the oxidation potential and reversibility for a large number of electroactive species may be found in *Encyclopedia of Electrochemistry of the Elements* (A. Bard and H. Lund eds., Marcel Dekker, New York). Other references identifying the oxidation for specific electroactive species include: for triphenylmethane, J. Perichon, M. Herlem, F. Bobilliart, and A. Thiebault *Encyclopedia of Electrochemistry of the Elements* vol. 11, p. 163 (A. Bard and H. Lund eds., Marcel Dekker, New York, N.Y. 1978); for N-hydroxyphthalimide, Masui, M., Ueshima, T. Ozaki, S. *J. Chem. Soc. Chem. Commun.* 479–80 (1983); for tris(4-bromophenyl)amine, Dapperheld, S., Steckhan, E., Brinkhaus, K. *Chem. Ber.*, 124, 2557–67 (1991); for 2,2,6,6-tetramethylpiperdine-N-oxide ("TEMPO"), Semmelhack, M., Chou, C., and Cortes, D. *J. Am. Chem. Soc.*, 105, 4492–4 (1983); for 5,10,15,20-tetrakis (pentafluorophenyl)-21H, 23H-porphine iron(III) chloride ("Fe(III)TPFPP chloride"), Dolphin, D., Traylor, T., and Xie, L. *Acc. Chem. Res.*, 30, 251–9 (1997); and for various porphyrins, J. H. Fuhrhop, Porphyrins and Metalloporphyrins 593 (K. Smith, ed., Elsevier, N.Y., 1975).

Electroactive molecular species also are useful in the context of the oxidation of N-isopropyl glyphosate to form glyphosate. In that context, an electroactive molecular species preferably is adsorbed to a noble metal catalyst on a graphitic carbon support. In the presence of the graphitic carbon support, the electroactive molecular species has been found to increase the noble metal catalyst's glyphosate selectivity.

Examples of generally suitable electroactive molecular species include triphenylmethane; N-hydroxyphthalimide; Fe(III)TPFPP chloride, 2,4,7-trichlorofluorene; tris(4-bromophenyl)amine; 2,2,6,6-tetramethyl piperidine N-oxide (sometimes referred to as "TEMPO"); 5,10,15,20-tetraphenyl-21H,23H-porphine iron(III) chloride (sometimes referred to as "Fe(III)TPP chloride"); 5,10,15,20-tetraphenyl-21H,23H porphine nickel(II) (sometimes referred to as (Ni(II) TPP"), 4,4'-difluorobenzophenone, and phenothiazine. When the noble metal catalyst is being used to catalyze the oxidation of NMG to glyphosate, the most preferred electroactive molecular species include N-hydroxyphthalimide; tris (4-bromophenyl) amine; TEMPO; Fe(III)TPP chloride; and Ni(II) TPP.

Electroactive molecular species may be adsorbed to the noble metal catalyst using various methods generally known in the art. The electroactive molecular species may be added directly to the oxidation reaction mixture separately from the noble metal catalyst. For example, 2,2,6,6-tetramethyl piperidine N-oxide ("TEMPO") may be added to the reaction mixture without first being adsorbed to the noble metal catalyst. Using this method, the electroactive molecule adsorbs to the noble metal catalyst while in the reaction mixture. Alterna-tively, the electroactive molecular species is adsorbed to the noble metal catalyst before being added to the oxidation reaction mixture. Generally, the electroactive molecular species may be adsorbed to the catalyst using, for example, liquid phase deposition or gas phase deposition.

The oxidation reaction preferably is carried out in a batch reactor so that the reaction may be contained until the conversion to glyphosate is complete. Other types of reactors, however, such as continuous stirred tank reactors may also be used, although preferably: (1) there should be sufficient contact between the oxygen, N-substituted glyphosate reactant, and the catalyst; and (2) there should be adequate retention time for substantial conversion of the N-substituted glyphosate reactant to glyphosate.

The oxidative cleavage can be performed, if desired, in the presence of a solvent, for example, a water-containing solvent. It may also be performed in the presence of other chemical species, such as N-methyl glyphosate, aminomethylphosphonic acid ("AMPA"), and N-methyl-aminomethylphosphonic acid ("MAMPA"), which may arise in connection with the preparation of glyphosate.

H. Preparation of Glyphosate

In a preferred embodiment of the present invention, the N-acyl reaction product of the carboxymethylation reaction is converted to glyphosate or one of its salts or esters having the structure (I):

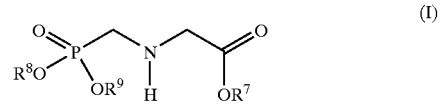

(I)

wherein $R^7$, $R^8$, and $R^9$ independently comprise hydrogen, hydrocarbyl, substituted hydrocarbyl, or an agronomically acceptable cation. When $R^7$, $R^8$, and $R^9$ of structure (I) are each hydrogen, structure (I) is glyphosate.

In general, the N-acyl reaction product may be converted to glyphosate when formaldehyde (or a formaldehyde source) is selected as the aldehyde and the carbamoyl compound is selected from among those compounds having the structure (II):

(II)

wherein $R^1$ is hydrocarbyl, substituted hydrocarbyl, or —$NR^3R^4$, $R^2$ and $R_{2a}$ are independently hydrogen, hydrocarbyl, or substituted hydrocarbyl, provided that —$NR^2R^{2a}$ can be carboxymethylated. Preferably, formalin is selected as the formaldehyde source; $R^1$ is alkyl or —$NR^3R^4$; $R^2$ and $R^3$ are independently hydrogen, alkyl, hydroxymethyl, amidomethyl, phosphonomethyl, carboxymethyl, or an ester or salt of carboxymethyl or phosphonomethyl; and $R^{2a}$ and $R^4$ are independently hydrogen, hydroxymethyl or another substituent which is hydrolyzable under the carboxymethylation reaction conditions. More preferably, $R^1$ is methyl, ethyl, isopropyl, or —$NR^3R^4$; $R^2$ and $R^3$ are independently hydrogen, methyl, ethyl, isopropyl, hydroxymethyl, carboxymethyl, phosphonomethyl or an ester or salt of carboxymethyl or phosphonomethyl; and $R^{2a}$ and $R^4$ are independently hydrogen or hydroxymethyl. Most preferably, $R^1$ is methyl or —$NR^3R^4$; $R^2$ and $R^3$ are independently hydrogen, methyl, hydroxymethyl, carboxymethyl, phosphonomethyl, or an ester or salt of carboxymethyl or phosphonomethyl; and $R^{2a}$ and $R^4$ are independently hydrogen or hydroxymethyl. Exemplary carbamoyl compounds thus include acetamide; urea; N-alkyl, N-phosphonomethyl, and N-carboxymethyl substituted acetamides; the esters and salts of N-phosphonomethyl and N-carboxymethyl substituted acetamides; N,N'-dialkyl, N,N'-diphosphonomethyl, and N,N'-dicarboxymethyl substituted ureas; the esters and salts of N,N'-diphosphonomethyl and N,N'-dicarboxymethyl substituted ureas; and amide equivalent compounds selected from the group consisting of cleavage and carboxymethylation catalyst recycle, as described elsewhere herein.

Preparation of Glyphosate from Acetamide

The preparation of glyphosate using acetamide as the carbamoyl compound is depicted in Reaction Scheme 6.

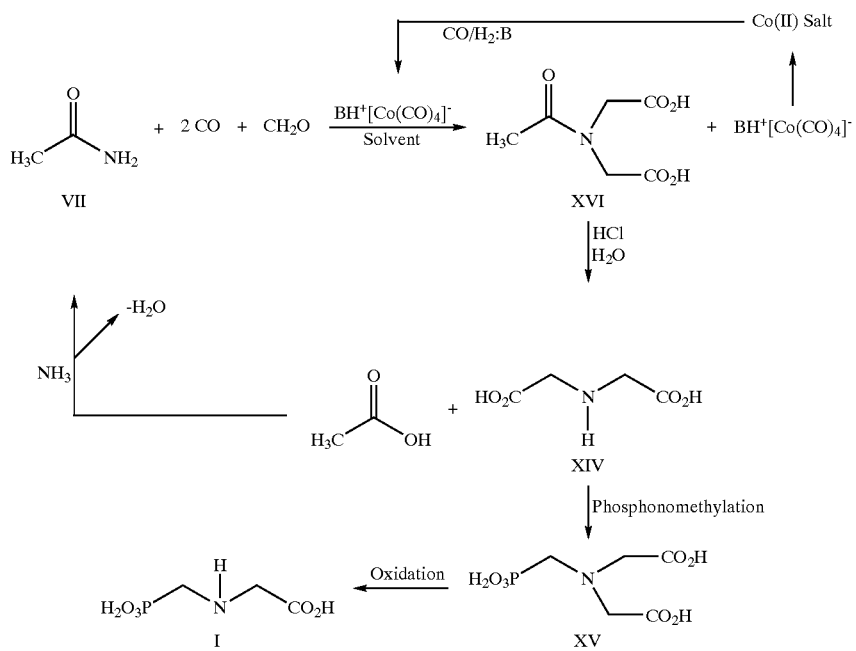

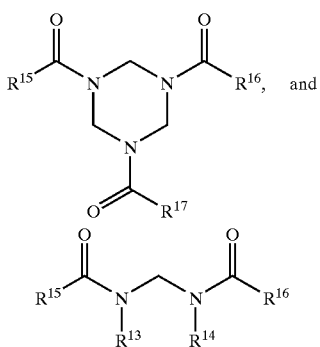

wherein $R^{13}$ and $R^{14}$ are independently hydrogen, hydroxymethyl, alkyl, carboxymethyl, phosphonomethyl, or an ester or salt of carboxymethyl or phosphonomethyl; and $R_{11}$, $R^{16}$ and $R^{17}$ are independently alkyl or —$NR^3R^4$. Preferred alkyl substituents for any of $R^{13}$, $R^{14}$, $R^{15}$, $R^{16}$ and $R^{17}$ are methyl, ethyl and isopropyl.

The sequence used to convert the N-acyl reaction product to glyphosate is dependent upon the starting carbamoyl compound. In general, however, the N-acyl group is hydrolyzed or otherwise removed from the N-acyl reaction product and, if the carbamoyl compound did not contain an N-phosphonomethyl substituent, the reaction product is phosphonomethylated either simultaneously with or subsequent to deacylation to remove the N-acyl substituent. Additional steps which can be employed include oxidative As depicted, one equivalent of acetamide VII is reacted with two equivalents each of carbon monoxide and formaldehyde in the presence of a carboxymethylation catalyst precursor and solvent; under these conditions the acetamide is protonated and forms a base pair (designated as $BH^+[Co(CO)_4]^-$) with the carboxymethylation catalyst precursor. The reaction produces N-acetyliminodiacetic acid XVI and a carboxymethylation catalyst reaction product ($BH^{30}$ [Co(CO)$_4$]$^-$ wherein "B" is acetamide).

In the presence of water and an acid such as hydrochloric acid, N-acetyliminodiacetic acid XVI is hydrolyzed to form iminodiacetic acid XIV and acetic acid. The separated iminodiacetic acid XIV is reacted with formaldehyde and $H_3PO_3$, $PCl_3$ or other $H_3PO_3$ source to produce N-(phosphonomethyl) iminodiacetic acid XV which is oxidized in the presence of a carbon or platinum on carbon catalyst to yield glyphosate I.

The cobalt used in the carboxymethylation step of the reaction can be recovered as a cobalt(II) salt as previously described in Section C. In addition, regenerating the cobalt (II) salt in the presence of acetamide (:B), carbon monoxide and hydrogen results in the formation of the base pair which is recycled to the carboxymethylation reaction mixture.

Similarly, the acetic acid which is generated by the hydrolysis of N-acetyliminodiacetic acid XVI to iminodiacetic acid XIV may be reacted with ammonia to form acetamide and recycled for use as a starting material in the carboxymethylation reaction. As a result, high atom efficiency is achieved by converting ammonia, carbon monoxide and formaldehyde into iminodiacetic acid.

In a preferred embodiment in which the amide is acetamide or an acetamide equivalent (that is, a composition which can be hydrolyzed to acetamide under the carboxymethylation reaction conditions), the reaction mixture for the carboxymethylation reaction contains acetic acid as an organic acid co-catalyst. Acetic acid, when used as a co-catalyst, has been found to provide the following surprising and significantly beneficial results:

1) certain ratios of cobalt to acetic acid in the carboxymethylation reaction mixture increases the yield of the N-acyl amino carboxylic acid reaction product;
2) the preferred ratio of cobalt to acetic acid exhibits a pressure dependency;
3) the presence of acetic acid results in an unexpected ability to increase yield of the N-acyl amino carboxylic acid reaction product by increasing pressure (typically, increases in pressure will lead to increased reaction rates but not yield); and
4) the increase in yields which is attainable by increases in pressure allows for an increase in payload.

As a result, high yields of N-acetyliminodiacetic acid (XVI) can be obtained at relatively high payloads.

In accordance with the present invention, the molar ratio of acetic acid to cobalt is generally in the range of about 2 to about 60, preferably about 7 to about 55, and still more preferably about 10 to about 50. At relatively lower pressures, for example, pressures less than about 1,800 psi (12,500 kPa), the molar ratio of acetic acid to cobalt is generally in the range of about 2 to about 20, preferably about 7 to about 15, and still more preferably about 11 to about 13. At intermediate pressures, for example, pressures within the range of about 1,800 to about 2,500 psi (12,500 to about 17,250 kPa), the molar ratio of acetic acid to cobalt is generally in the range of about 2 to about 45, preferably about 8 to about 30, and still more preferably about 10 to about 20. At relatively high pressures, for example, pressures of at least about 2,500 psi (17,250 kPa), the molar ratio of acetic acid to cobalt is generally in the range of about 4 to about 60, preferably about 8 to about 55, and still more preferably about 10 to about 50. The surprising effect of using acetic acid on the carboxymethylation of acetamide (VII), is illustrated in Example 22 and the table associated therewith which shows the percent yield of N-acetyliminodiacetic acid (XVI) based on starting amount of acetamide (VII) under different reaction conditions of pressure, payload, solvent, added water, amount of $Co_2(CO)_8$ catalyst precursor, and added acetic acid co-catalyst.

The experimental data obtained to date further suggests that yield is surprisingly improved when acetic acid is used as a co-catalyst in the carboxymethylation of acetamide (VII) when water is present in the reaction mixture. This effect is illustrated in the table which appears in association with Example 23 which shows the percent yield of N-acetyliminodiacetic acid (XVI) based on starting amount of acetamide (VII) when HOAc/Co ratio is varied against moles $H_2O$. Reaction conditions included 1500 psi $CO:H_2$ (95:5), 90 mL DME solvent, 11.8 g acetamide, 13.6 g of 95% paraformaldehyde, and 4.1 g $Co_2(CO)_8$. Typically, the molar ratio of water to acetamide starting material is about 1 to about 5, preferably about 2 to about 4, and more preferably about 3.2 to about 3.8.

As illustrated in Example 24, the yield of N-acetyliminodiacetic acid surprisingly increases with increasing pressure. Conventionally, reaction rates, not yields increase with increasing pressure. Accordingly, if lesser catalyst loads or greater payloads are desired for the reaction mixture, it is preferred that the carboxymethylation reaction of acetamide be carried out at a pressure of at least about 500 psi (3,500 kPa), more preferably at least about 1,500 psi (10,500 kPa), and most preferably about 3,000 to about 3,500 psi (21,000–24,000 kPa).

Example 25 further illustrates that an increase in pressure allows for an increase in payload. For a given catalyst load, increasing pressure permits an increase in payload while maintaining high, commercially acceptable yields of N-acetyliminodiacetic acid. Thus, for example, increasing pressure from 1,500 psi (10,340 kPa) to 3,200 psi (22,000 kPa) allows the payload to be doubled without a loss in yield, whereas a doubling of payload at 1,500 psi (10,340 kPa) results in a significant loss of yield.

An alternative route for the preparation of glyphosate I from acetamide VII is illustrated in Reaction Scheme 7:

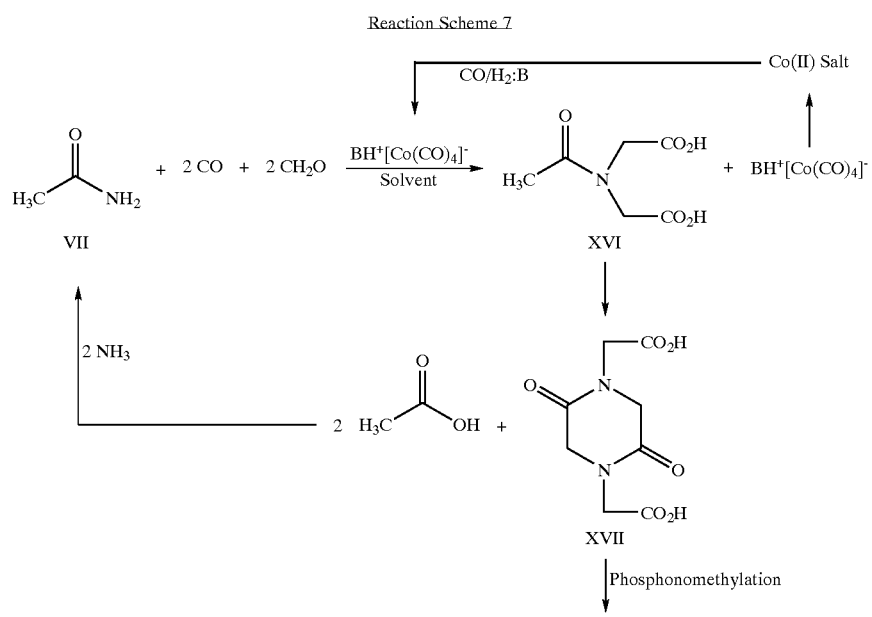

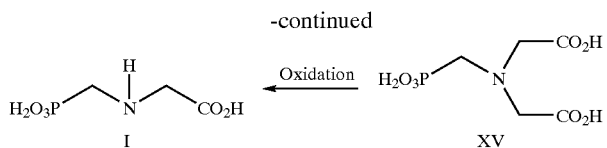

In general, the sequence of reactions in Reaction Scheme 7 is the same as those in Reaction Scheme 6 except that N-acetyliminodiacetic acid XVI is deacylated to form 1,4-di(carboxymethyl)-2,5-diketopiperazine XVII which is then directly phosphonomethylated in the same manner as iminodiacetic acid XIV is phosphonomethylated in Reaction Scheme 6.

A third alternative reaction scheme for the preparation of glyphosate I from acetamide VII is depicted in Reaction Scheme 8:

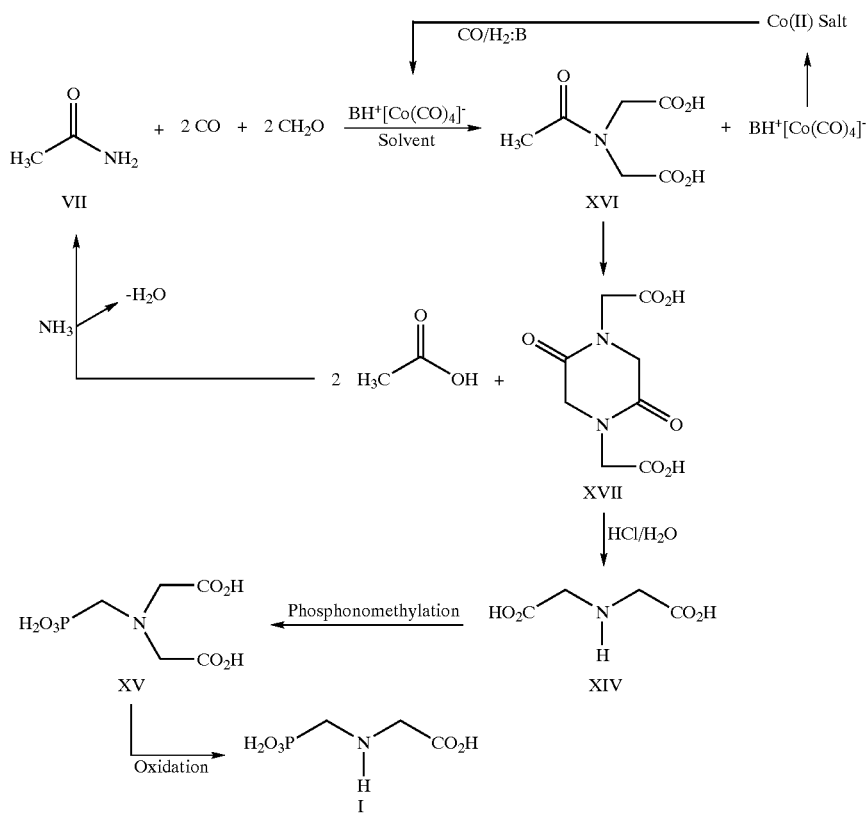

In general, the sequence of reactions in Reaction Scheme 8 is the same as those in Reaction Scheme 7 except that 1,4-di(carboxymethyl)-2,5-diketopiperazine XVII is hydrolyzed using water and an acid such as hydrochloric acid to iminodiacetic acid XIV which is then phosphonomethylated as described in Reaction Scheme 6.

A fourth alternative reaction scheme for the preparation of glyphosate I from acetamide VII is depicted in Reaction Scheme 9:

Reaction Scheme 9

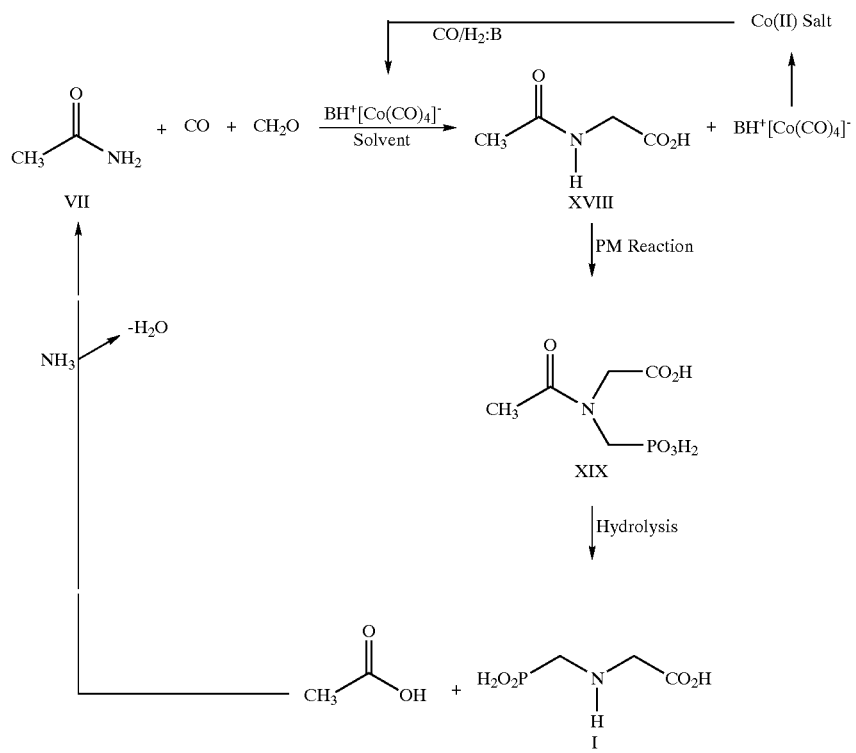

As depicted in Reaction Scheme 9, one equivalent of acetamide VII is reacted with one equivalent each of carbon monoxide and formaldehyde in the presence of a carboxymethylation catalyst precursor and solvent to yield N-acetylglycine XVIII. In this reaction sequence, the formation of the base pair, and recycle and regeneration of the cobalt(II) salt are as described in connection with Reaction Scheme 6.

In contrast to Reaction Scheme 6, however, N-acetylglycine XVIII is reacted with formaldehyde and $H_3PO_3$, $PCl_3$ or other $H_3PO_3$ source to produce N-(phosphonomethyl)-N-acetylglycine XIX which is hydrolyzed using water and an acid such as hydrochloric acid to produce Glyphosate I and acetic acid. Acetic acid which is produced in the hydrolysis step can be reacted with ammonia to generate acetamide for the carboxymethylation step.

A fifth alternative reaction scheme for the preparation of glyphosate I from acetamide VII is depicted in Reaction Scheme 9a:

Reaction Scheme 9a

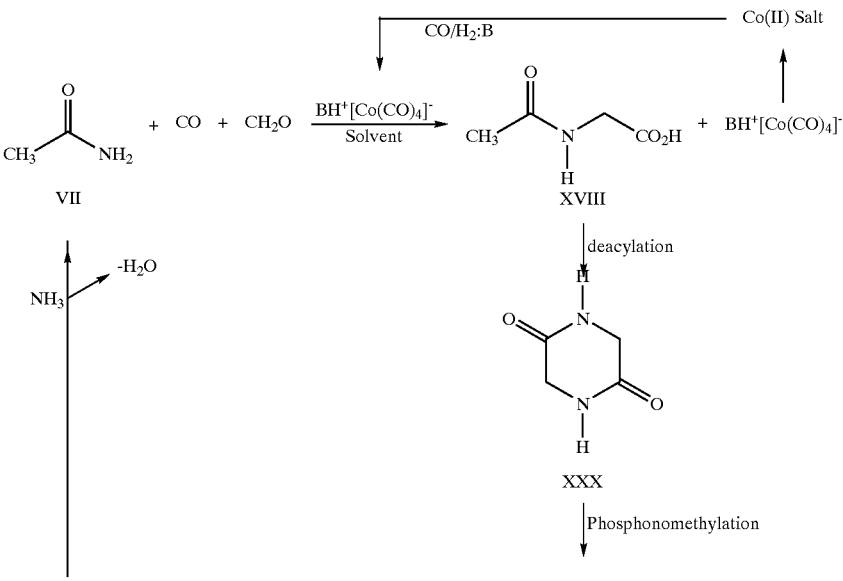

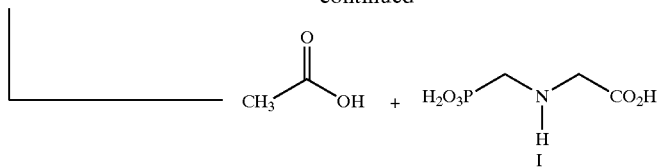

The sequence of reactions in Reaction Scheme 9a is comparable to those set forth in Reaction Scheme 9 except that N-acetylglycine XVIII is deacylated to form 2,5-diketopiperazine XXX. 2,5-diketopiperazine XXX is then reacted with formaldehyde and $H_3PO_3$, $PCl_3$ or other $H_3PO_3$ source to produce N-(phosphonomethyl)glycine I and acetic acid. Acetic acid which is produced in the hydrolysis step can be reacted with ammonia to generate acetamide for the carboxymethylation step.

Instead of starting with acetamide in the forgoing reaction schemes, an acetamide equivalent may be used. As used herein, an acetamide equivalent is a composition which, upon hydrolysis, yields acetamide or hydroxymethyl acetamide. Examples of acetamide equivalents include the following compositions:

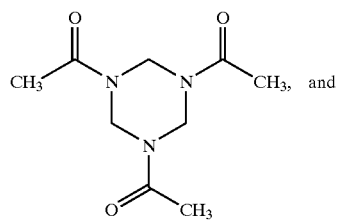

XXV

-continued

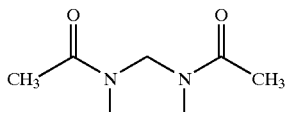

VI

Thus, for example, these compounds may be substituted for acetamide in any one of Reaction Schemes 6, 7, 8, 9 and 9a.

Preparation of Glyphosate from N-methylacetamide

The preparation of N-(phosphonomethyl)glycine using N-methyl acetamide as the carbamoyl compound is depicted in Reaction Scheme 10:

Reaction Scheme 10

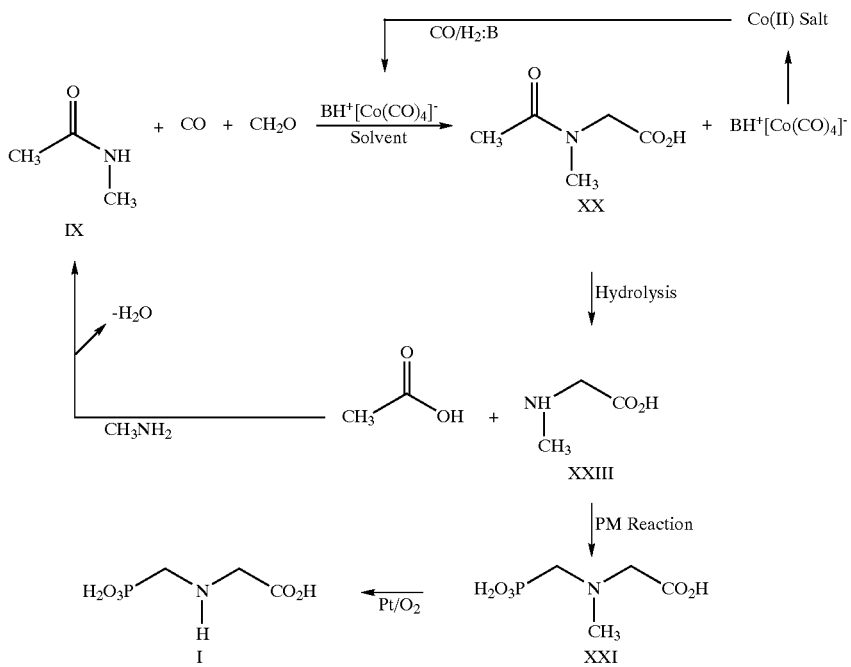

As depicted, one equivalent of N-methylacetamide IX is reacted with one equivalent each of carbon monoxide and formaldehyde in the presence of a carboxymethylation catalyst precursor and solvent to yield N-acetylsarcosine XX. In the presence of water and an acid such as hydrochloric acid, N-acetylsarcosine XX is hydrolyzed to sarcosine XXIII and acetic acid. Sarcosine XXIII is reacted with formaldehyde and $H_3PO_3$, $PCl_3$ or other $H_3PO_3$ source to produce N-(phosphonomethyl)-N-methyl-glycine XXI which is oxidized in the presence of a platinum catalyst and oxygen to glyphosate I.

Similar to the preparation of glyphosate from acetamide as described in connection with Reaction Scheme 6, the carboxymethylation catalyst reaction product (BH⁺[Co(CO)₄]⁻ wherein "B" is N-methylacetamide) is recycled and then regenerated in the presence of N-methylacetamide.

Also, acetic acid which is generated by the hydrolysis of N-acetylsarcosine XX to sarcosine XXIII is reacted with methylamine to form N-methylacetamide and recycled for use as a starting material in the carboxymethylation reaction.

An alternative route for the preparation of glyphosate I from N-methylacetamide IX is illustrated in Reaction Scheme 11:

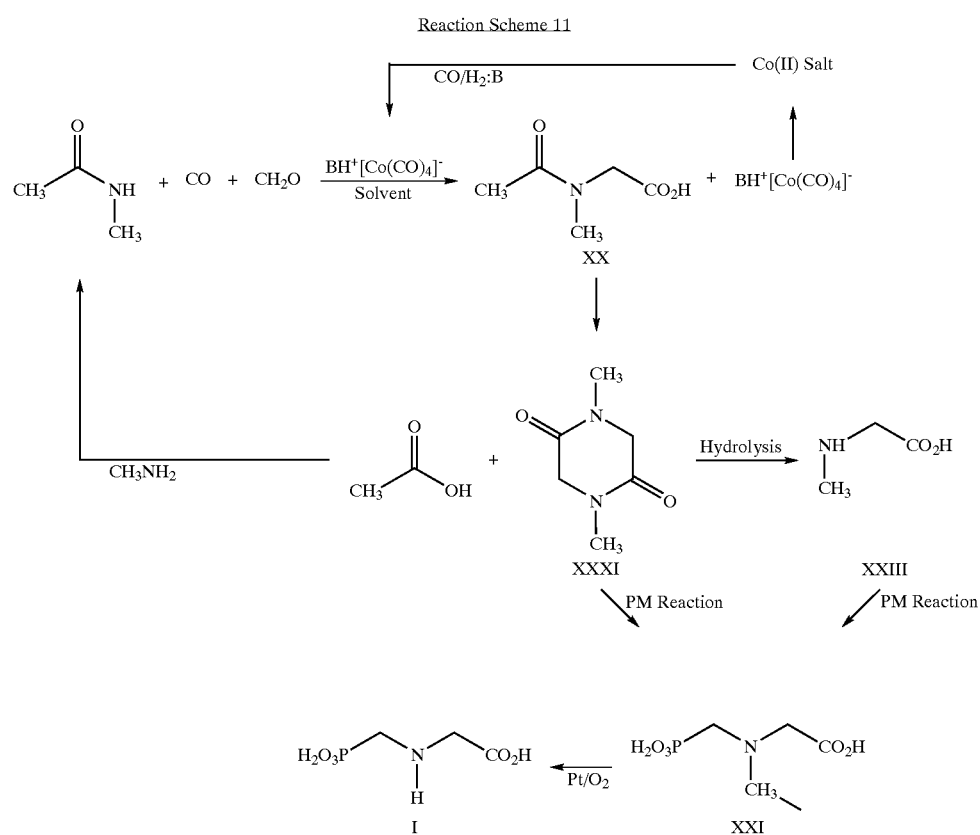

Reaction Scheme 11

In general, the sequence of reactions in Reaction Scheme 11 is the same as those in Reaction Scheme 10 except that N-acetylsarcosine XX is deacylated to form 1,4-dimethyl-2,5-diketopiperazine XXXI. 1,4-dimethyl-2,5-diketopiperazine XXXI is then directly phosphonomethylated in the same manner as sarcosine XXIII is phosphonomethylated in Reaction Scheme 10. Alternatively, 1,4-dimethyl-2,5-diketopiperazine XXXI is hydrolyzed to sarcosine XXIII and phosphonomethylated as described in connection with Reaction Scheme 10.

A third alternative reaction scheme for the preparation of glyphosate I from N-methylacetamide IX is depicted in Reaction Scheme 12:

Reaction Scheme 12

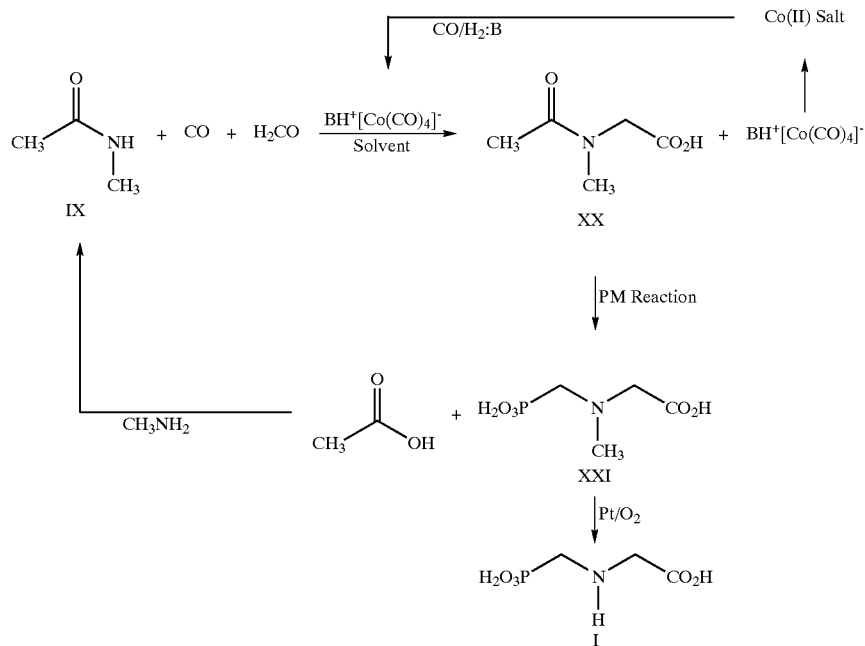

As depicted, the carboxymethylation step of Reaction Scheme 12 is the same as the carboxymethylation step of Reaction Schemes 10 and 11. In Reaction Scheme 12, however, N-acetylsarcosine XX is reacted with formaldehyde and $H_3PO_3$, $PCl_3$ or other $H_3PO_3$ source to produce N-(phosphonomethyl)-N-methyl-glycine XXI which is oxidized in the presence of a platinum catalyst and oxygen to Glyphosate I and acetic acid. The acetic acid is then reacted with methylamine to yield the N-methylacetamide starting material.

Preparation of Glyphosate from N-acetglycine XVIII

The preparation of N-(phosphonomethyl)glycine starting from N-acetglycine XVIII is depicted in Reaction Schemes 13 and 14. In this Reaction Scheme, N-acetglycine XVIII is carboxymethylated to yield N-acetyliminodiacetic acid XVI which is then converted to Glyphosate I as described in Reaction Schemes 6, 7, and 8.

Acetic acid is produced as a hydrolysis product in each of Reaction Schemes 13 and 14. The acetic acid is reacted with ammonia to generate acetamide VII which can then be carboxymethylated to make compound XVIII.

Reaction Scheme 13

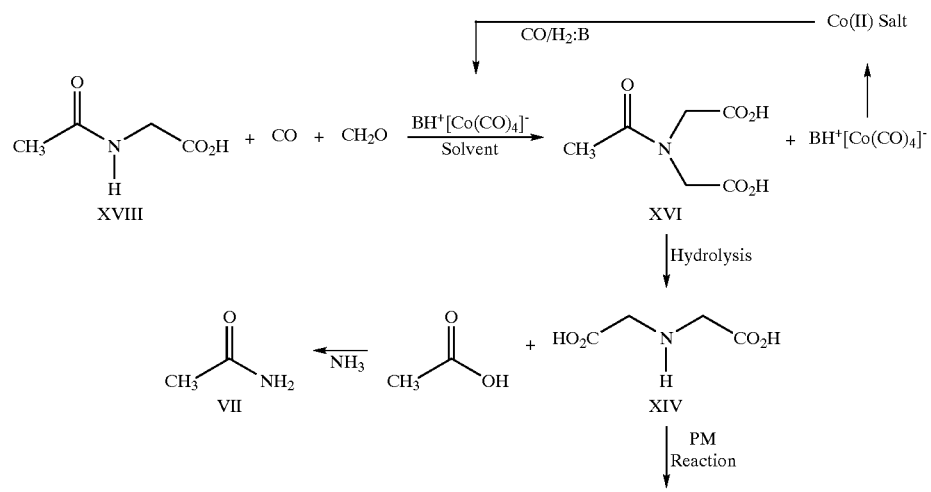

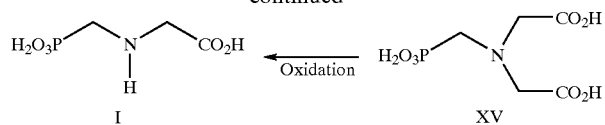

Reaction Scheme 14

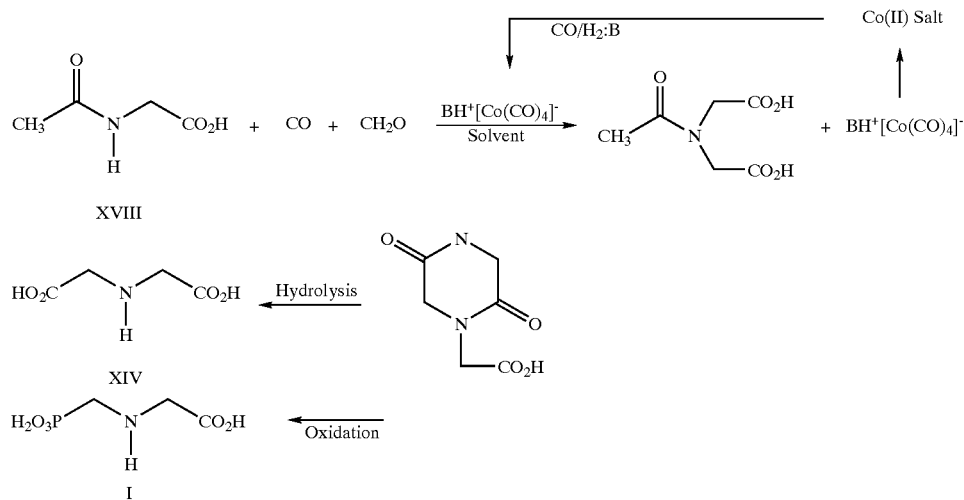

Preparation of Glyphosate from N-methylacetamide Equivalent

The preparation of N-(phosphonomethyl)glycine using VIII which is an N-methylacetamide equivalent is depicted in Reaction Schemes 15 and 16. Thus, VIII is carboxymethylated to form N-methyl-N-acetylglycine XX which is converted to Glyphosate I as described in Reaction Schemes 10, 11 and 12.

Reaction Scheme 15

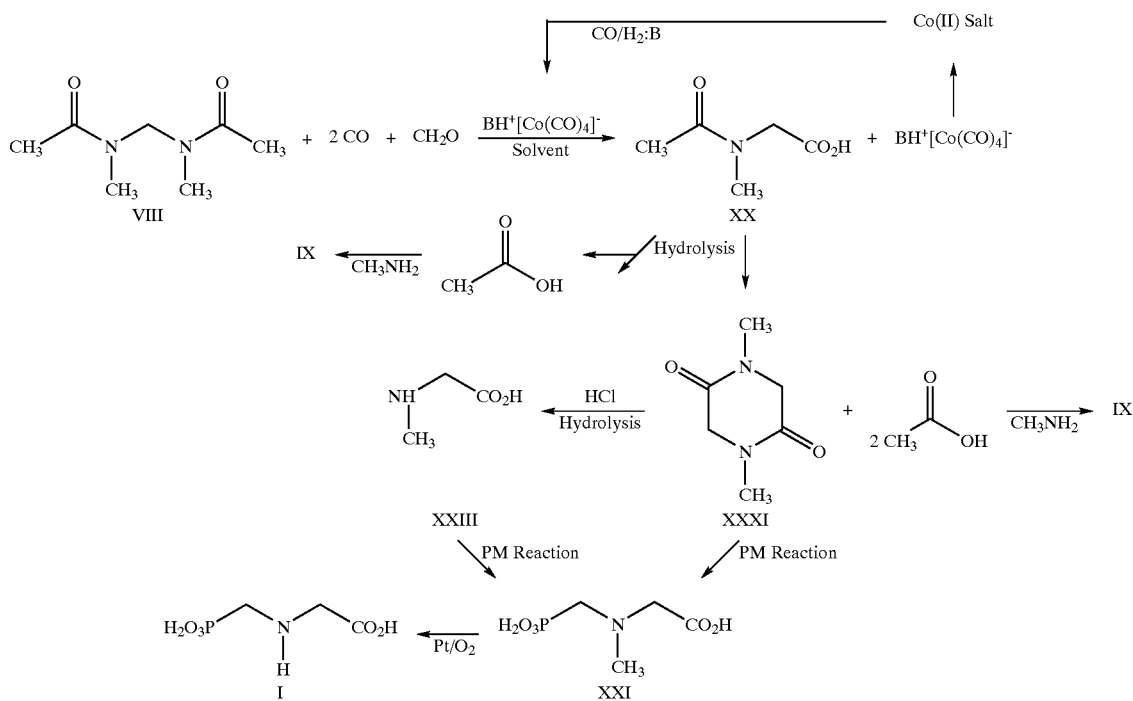

Reaction Scheme 16
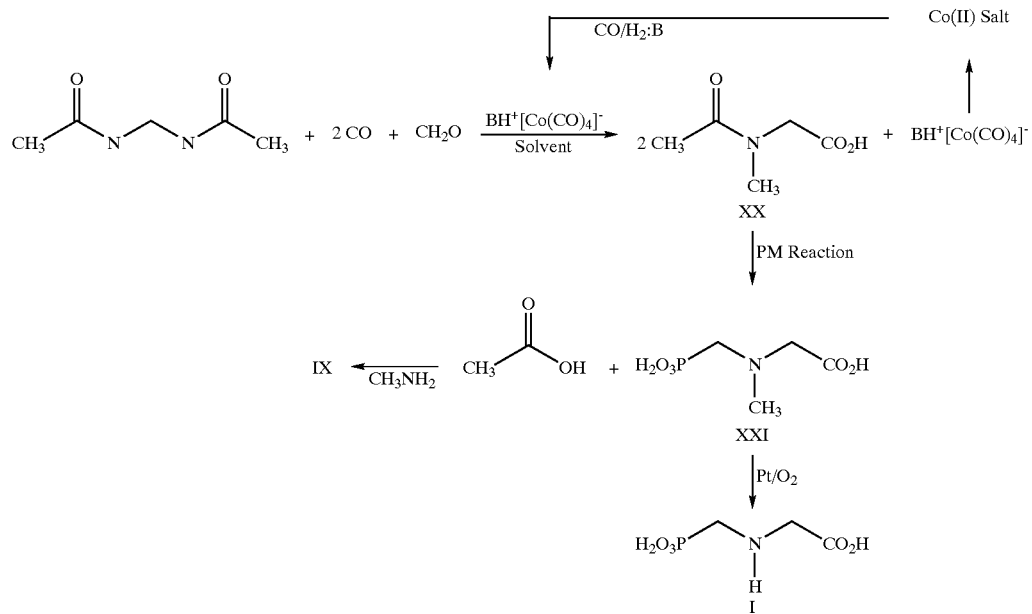
Preparation of Glyphosate from Urea
The preparation of N-(phosphonomethyl)glycine from urea is depicted in Reaction Scheme 17:
Reaction Scheme 17
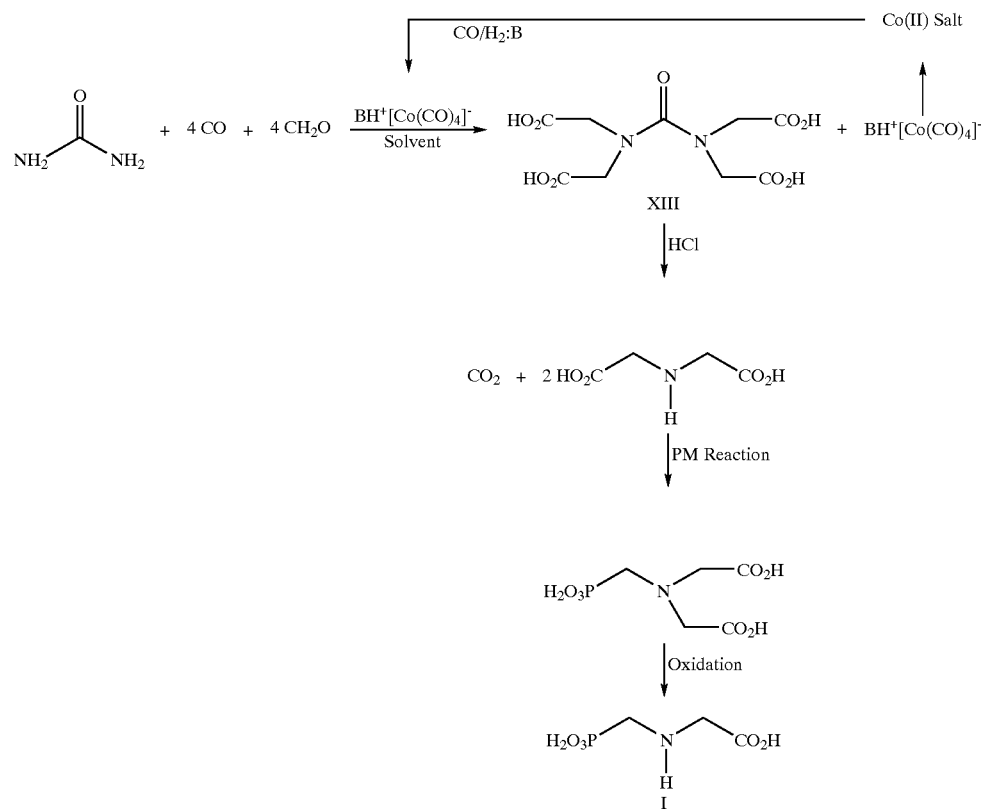

As depicted, one equivalent of urea V is reacted with four equivalents each of carbon monoxide and formaldehyde in the presence of a carboxymethylation catalyst precursor and solvent. In contrast to Reaction Scheme 6, in this Reaction Scheme urea V is reacted with the carboxymethylation catalyst precursor in the absence of formalin to form the base pair $(BH^+[Co(CO)_4]^-)^{31}$ wherein B is urea).

The products of the carboxymethylation reaction are the tetraacid XIII and the carboxymethylation catalyst reaction product $(BH^+[Co(CO)_4]^-$ wherein "B" is urea). Tetraacid XIII is hydrolyzed to 2 equivalents of iminodiacetic acid XIV and carbon dioxide and iminodiacetic acid XIV is converted to Glyphosate I as described in connection with Reaction Schemes 6 and 8.

Preparation of Glyphosate from N,N-dimethylUrea

The preparation of N-(phosphonomethyl)glycine from N,N-dimethylurea is depicted in Reaction Scheme 18:

formaldehyde in the presence of a carboxymethylation catalyst precursor and solvent. Similar to Reaction Scheme 18, in this reaction scheme N,N-dimethylurea X is reacted with the carboxymethylation catalyst precursor in the absence of formalin to form the base pair $(BH^+[Co(CO)_4]^-)$ wherein $BH^+$ is the protonated N,N'-dimethylurea X.

The products of the carboxymethylation reaction are the diacid XXII and the carboxymethylation catalyst reaction product $(BH^+[Co(CO)_4]^-$ wherein B is N,N'-dimethylurea). Diacid XXII is hydrolyzed to 2 equivalents of sarcosine XXIII and carbon dioxide and sarcosine XXIII is converted to Glyphosate I as described in connection with Reaction Schemes 10 and 15.

An alternative method for the preparation of N-(phosphonomethyl)glycine I from N,N'-dimethylurea X is depicted in Reaction Scheme 19:

Reaction Scheme 18

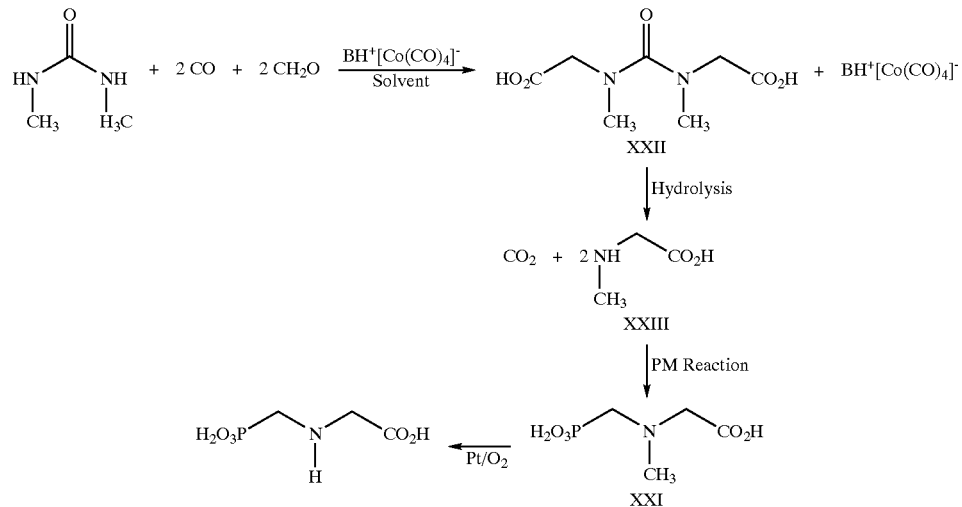

As depicted, one equivalent of N,N-dimethylurea X is reacted with two equivalents each of carbon monoxide and Reaction Scheme 19

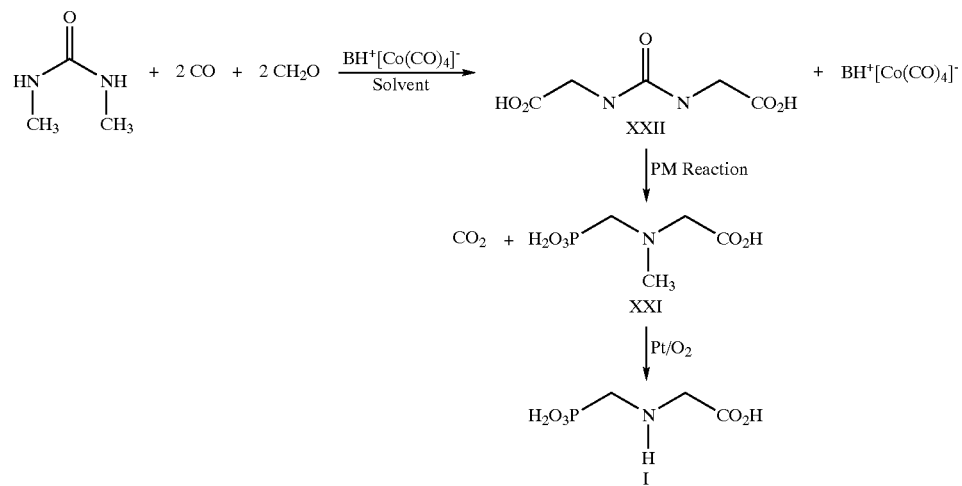

As depicted, the carboxymethylation reaction is carried out as described in connection with Reaction Scheme 18 to yield diacid XXII and the carboxymethylation catalyst reaction product $(BH^+[Co(CO)_4]^-$ wherein "B" is N,N'-dimethylurea). In this reaction scheme, however, diacid XXII is reacted with formaldehyde and $H_3PO_3$, $PCl_3$ or other $H_3PO_3$ source to produce N-(phosphonomethyl)-N-methyl-glycine XXI which is oxidized in the presence of a platinum catalyst and oxygen to glyphosate I.

Preparation of Glyphosate from Bis-Phosphonomethylurea

The preparation of N-(phosphonomethyl)glycine from bis-phosphonomethylurea XII is depicted in Reaction Scheme 20:

Reaction Scheme 20

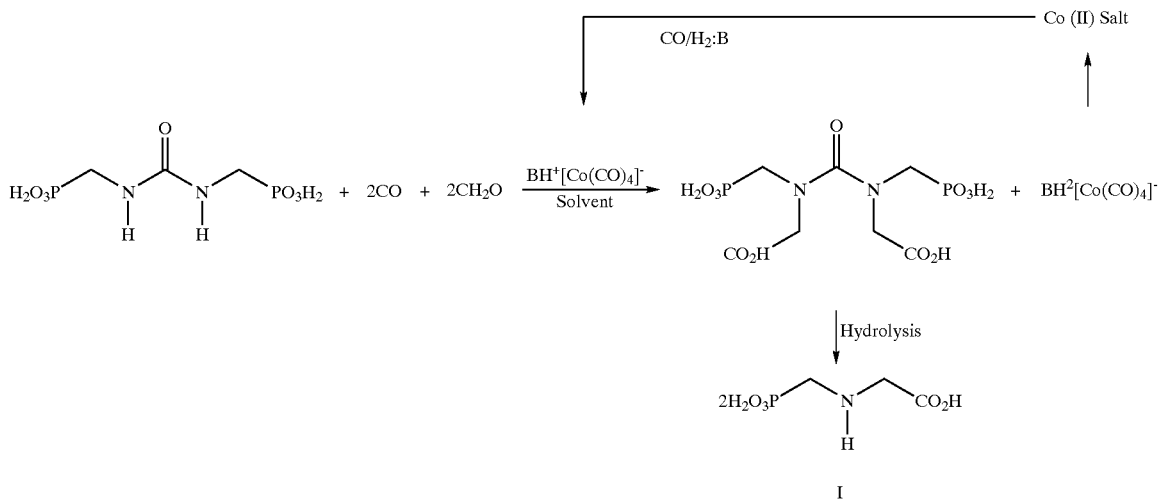

As depicted, one equivalent of bis-phosphonomethylurea XII is reacted with two equivalents each of carbon monoxide and formaldehyde in the presence of a carboxymethylation catalyst precursor and solvent. In this reaction scheme bis-phosphonomethylurea XII is reacted with the carboxymethylation catalyst precursor in the absence of formalin to form the base pair $(BH^+[Co(CO)_4]^-)$ wherein $BH^+$ is the protonated bis-phosphonomethylurea XII.

The products of the carboxymethylation reaction are XXIV and the carboxymethylation catalyst reaction product $(BH^+[Co(CO)_4]^-$ wherein "B" is bisphosphonomethylurea). XXIV is hydrolyzed in the presence of a hydrolysis catalyst (preferably an acid or base, and more preferably a mineral acid) to form N-(phosphonomethyl) glycine I.

Preparation of Glyphosate from N-acetyl-N-phosphonomethylamine

The preparation of N-(phosphonomethyl)glycine I from N-acetyl-N-phosphonomethylamine XI is depicted in Reaction Scheme 21:

Reaction Scheme 21

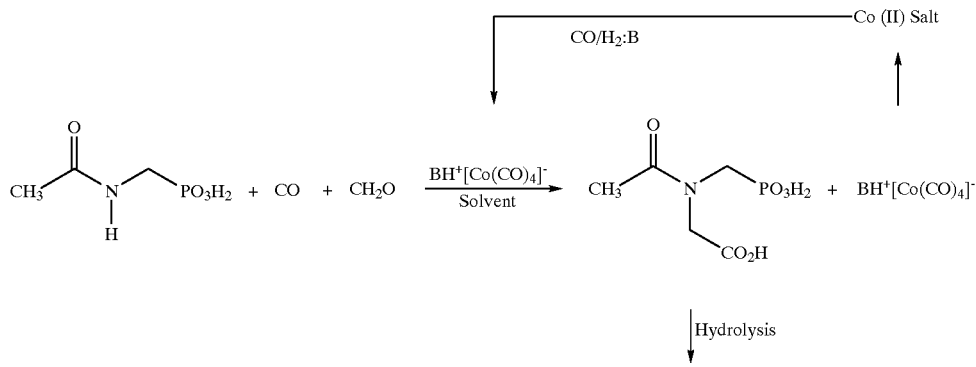

-continued

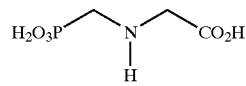

I

As depicted, one equivalent of N-acetyl-N-phosphonomethylamine XI is reacted with one equivalent each of carbon monoxide and formaldehyde in the presence of a carboxymethylation catalyst precursor and solvent. In this reaction scheme N-acetyl-N—phosphonomethylamine is reacted with the carboxymethylation catalyst precursor in the absence of formalin to form the base pair (BH$^+$[Co(CO)$_4$]$^-$) wherein BH$^+$ is the protonated N-acetyl-N-phosphonomethylglycine XI.

The products of the carboxymethylation reaction are XIX and the carboxymethylation catalyst reaction product (BH$^+$[Co(CO)$_4$]$^-$ wherein "B" is N-acetyl-N-phosphonomethylamine). XIX is hydrolyzed in the presence of a hydrolysis catalyst (preferably an acid or base, and more preferably a mineral acid) to form N-(phosphonomethyl) glycine I.

Definitions

The following definitions are provided in order to aid the reader in understanding the detailed description of the present invention:

"Glyphosate" means N-(phosphonomethyl) glycine in acid form or any of its salt or ester forms.

"Hydrocarbyl" means a group composed of carbon and hydrogen. This definition includes alkyl, alkenyl, and alkynyl groups which are each straight chain, branched chain, or cyclic hydrocarbons from one to about twenty carbons. Also included in this definition are aryl groups composed of carbon and hydrogen. Hydrocarbyl therefore includes, for example, methyl, ethyl, propyl, butyl, pentyl, hexyl, cyclopropyl, cyclobutyl, cyclopentyl, cyclohexyl, methylcyclopentyl, ethenyl, propenyl, butenyl, pentenyl, hexenyl, ethyne, propyne, butyne, pentyne, hexyne, phenyl, naphthyl, anthracenyl, benzyl, and isomers thereof.

"Substituted hydrocarbyl" means a hydrocarbyl group in which one or more hydrogen has been substituted with a heteroatom-containing group. Such substituent groups include, for example, halo, oxo, heterocycle, alkoxy, hydroxy, aryloxy, —NO$_2$, amino, alkylamino, or amido. When the substituent group is oxo, the substituted hydrocarbyl can be, for example, an acyl group.

"Heteroatom" means an atom of any element other than carbon or hydrogen which is capable of forming chemical bonds.

"Heterocycle" means a saturated or unsaturated mono- or multi-ring carbocycle wherein one or more carbon atoms is replaced by N, S, P, or O. This includes, for example, the following structures:

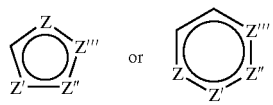

wherein Z, Z', Z", or Z''' is C, S, P, O, or N, with the proviso that one of Z, Z', Z", or Z''' is other than carbon, but is not O or S when attached to another Z atom by a double bond or when attached to another O or S atom. Furthermore, the optional substituents are understood to be attached to Z, Z', Z", or Z''' only when each is C. The point of attachment to the molecule of interest can be at the heteroatom or elsewhere within the ring.

"Halogen" or "halo" means a fluoro, chloro, bromo, or iodo group.

"Carbamoyl" means a group containing a fully saturated nitrogen atom attached by a single bond to a carbonyl moiety.

"Carboxymethyl" means a group containing a carboxylate moiety attached by the carboxylate carbon atom to a saturated carbon atom which in turn is attached to the molecule of interest.

"Carboxymethylation catalyst" means a catalyst which is useful in carbonylation reactions, and particularly in carboxymethylation reactions.

"Carboxymethylation" means the introduction of a substituted or unsubstituted carboxymethyl group into the molecule of interest.

"Payload" means the mass of starting material divided by the mass of reaction solvent.

"PM" means phosphonomethylation.

"GC" means gas chromatography.

"HPLC" means high pressure liquid chromatography.

"IC" means ion chromatography.

"NMR" means nuclear magnetic resonance spectroscopy.

"MS" means mass spectrometry.

The following examples will illustrate the invention.

EXAMPLES

In the representative examples below of carboxymethylation, either a 300 or 2000 mL stainless steel autoclave equipped with a magnetic stirrer and heating system was employed. All compound numbers are in Roman numerals and reflect the structures which appear in Reaction Schemes 1–21. The progress of the reaction was monitored by following the consumption of gas. At the end of each heating period the reaction mixture was cooled to ambient temperature before analysis. N-Acetyliminodiacetic acid (XVI) was quantified by HPLC analysis utilizing an Interaction Ion 310 ion exclusion column at 30° C. and UV absorption detection at 210 nm. The 0.04 N H$_2$SO$_4$ mobile phase pumped at 0.5 mL/min. gave retention times from 4.6–4.8 min. for (XVI). All yields are based on moles of acetamide charged.

Example 1

Example 1 and 2 illustrate that increasing the reaction pressure has no effect on yield of (XVI) when using HCl as a co-catalyst.

A 300 mL autoclave was charged with acetamide (VII) (11.8 g, 0.2 mole), 95% paraformaldehyde (13.6 g, 0.43 mole), water (12.9 g, 0.72 mole), 37% HCl (1.8 g, 0.018 mole), DME (90 mL), and Co$_2$(CO)$_8$ (4.1 g, 0.012 mole) and pressurized to 1500 psi (10,345 kPa) CO at 25° C. This mixture was heated to 110° C. for 30 minutes. HPLC analysis of this stream gave an 87% yield of (XVI), 0.5% iminodiacetic acid (XIV), and 4.0% N-acetylglycine (XVIII).

Example 2

A 300 mL autoclave was charged with acetamide (VII) (11.8 g, 0.2 mole), 95% paraformaldehyde (13.6 g, 0.43 mole), water (12.9 g, 0.72 mole), 37% HCl (1.8 g, 0.018 mole), DME (90 mL), and $Co_2(CO)_8$ (4.1 g, 0.012 mole) and pressurized to 4000 psi (27,580 kPa) CO at 25° C. This mixture was heated to 110° C. for 30 min. HPLC analysis of this stream gave an 87% yield of (XVI), 0.5% (XIV), and 4.0% (XVIII).

Example 3

This example illustrates a typical reaction in the absence of added acetic acid.

A 300 mL autoclave was charged with acetamide (VII) (11.8 g, 0.2 mole), 95% paraformaldehyde (13.6 g, 0.43 mole), water (12.9 g, 0.72 mole), DME (90 mL), and $Co_2(CO)_8$ (4.1 g, 0.012 mole) and pressurized to 1500 psi (10,345 kPa) $CO:H_2$ (95:5) at 25° C. for 30 min. HPLC analysis of this stream gave an 89% yield of (XVI), 1% (XIV), and 8% (XVIII).

Example 4

This example illustrates the unexpected increase in yield of (XVI) observed when a specific mole ratio of acetic acid to cobalt catalyst is maintained at 1500 psi (10,345 kPa). A typical reaction is described below. Summarized in Table 1 and FIG. 1 are the results of reactions run under identical conditions as described below but with varying amounts of added acetic acid. An autoclave was charged with acetamide (VII) (11.8 g, 0.2 mole), 95% paraformaldehyde (13.6 g, 0.43 mole), water (12.9 g, 0.72 mole), acetic acid (5.4 g, 0.09 mole), dimethoxyethane (DME) (90 mL), and $Co_2(CO)_8$ (4.1 g, 0.012 mole) and pressurized to 1500 psi (10,345 kPa) $CO:H_2$ (95:5) at 25° C. This mixture was heated to 125° C. for 30 min. The reaction was allowed to cool to room temperature. HPLC analysis of the reaction gave a 92% yield of (XVI), 1% (XIV), and 7% (XVIII).

TABLE 3

Yield vs. added acetic acid at 1500 psi (10,345 kPa)

| Acetic acid (g) | Acetic Acid (moles) | Cobalt (moles)[b] | Mole Ratio Acetic acid/Co | % Yield (XVI) |
|---|---|---|---|---|
| 0[a] | 0 | 0.024 | — | 89 |
| 5.4 | 0.09 | 0.024 | 3.7 | 92 |
| 10.6 | 0.17 | 0.024 | 7.0 | 92 |
| 16.8 | 0.28 | 0.024 | 11.6 | 93 |
| 18.0 | 0.30 | 0.024 | 12.5 | 98 |
| 21.6 | 0.36 | 0.024 | 15.0 | 81 |

[a]From Example 3.
[b]Expressed as the number of moles of cobalt atoms. Cobalt was supplied as $Co_2(CO)_8$.

Example 5

Figure 2:
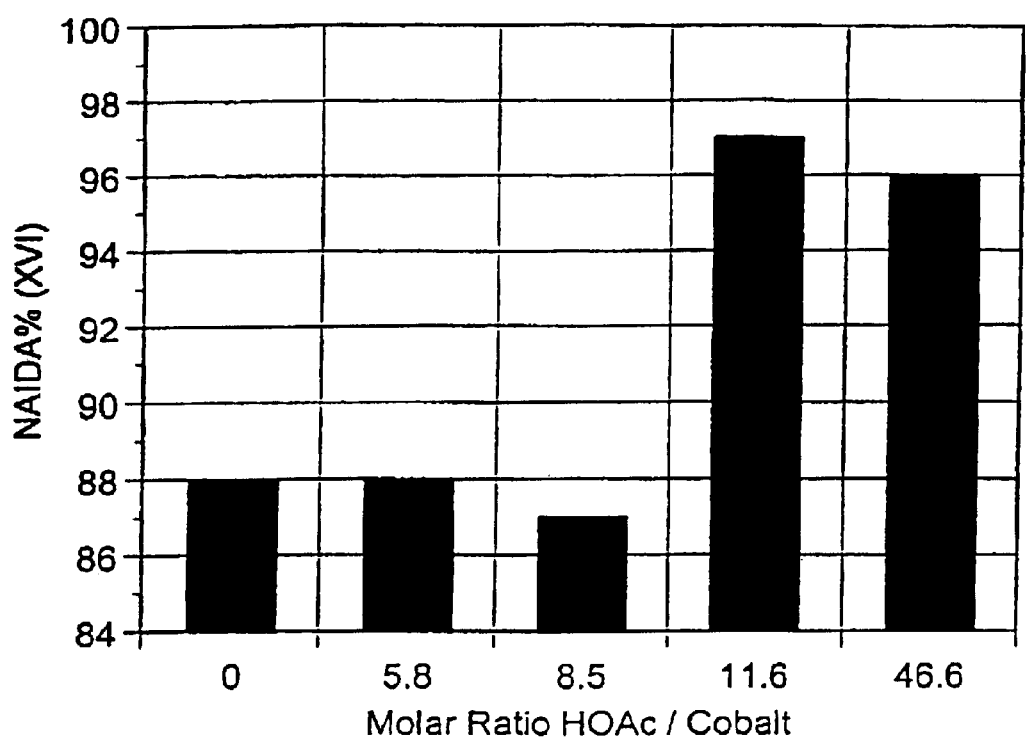
FIG. 2 is a graph of the molar ratio of acetic acid to cobalt versus the yield of N-acetyliminodiacetic acid (XVI) under the conditions described in Example 5.

This example illustrates that the optimal mole ratio of acetic acid to cobalt needed to achieve high yields of (XVI) varies with reaction pressure. A typical reaction is described below where the reaction was conducted at 3200 psi (22,069 kPa). Summarized in Table 4 and FIG. 2 are the results of reactions run under identical conditions as described below but with various amounts of added acetic acid.

An autoclave was charged with acetamide (VII) (11.8 g, 0.2 mole), 95% paraformaldehyde (13.6 g, 0.43 mole), water (12.9 g, 0.72 mole), acetic acid (4.2 g, 0.07 mole), tetrahydrofuran (THF) (90 mL), and $Co_2(CO)_8$ (1 g, 0.003 mole) and pressurized to 3200 psi (22,069 kPa) $CO:H_2$ (95:5) at 25° C. This mixture was heated to 125° C. for 30 min. The reaction was allowed to cool to room temperature. HPLC analysis of the reaction gave 97% yield of (XVI).

TABLE 4

Yield vs. added acetic acid at 3200 psi

| Acetic acid (g) | Acetic Acid (moles) | Cobalt (moles)[b] | Mole Ratio Acetic acid/Co | % Yield (XVI) |
|---|---|---|---|---|
| 0[a] | 0 | 0.006 | — | 89 |
| 2.1 | 0.035 | 0.006 | 5.8 | 88 |
| 3.1 | 0.051 | 0.006 | 8.5 | 87 |
| 4.2 | 0.07 | 0.006 | 11.6 | 97 |
| 16.8 | 0.28 | 0.006 | 46.6 | 96 |

[a]From Example 3.
[b]Expressed as the number of moles of cobalt atoms. Cobalt was supplied as $Co_2(CO)_8$.

Example 6

This example illustrates that the optimum acetic acid:cobalt mole ratio varies with reaction pressure.

A 300 mL autoclave was charged with acetamide (VII) (11.8 g, 0.2 mole), 95% paraformaldehyde (13.6 g, 0.42 mole), water (12.9 g, 0.72 mole), acetic acid (21.2 g, 0.33 mole, 0.24 g/mL of DME), DME (90 mL), and $Co_2(CO)_8$ (4.1 g, 0.012 mole) and pressurized to 2200 psi (15,170 kPa) $CO:H_2$ (95:5) at 25° C. This mixture was heated to 125° C. for 30 min. HPLC analysis of this stream gave a 95% yield of (XVI), 1% (XIV), and 3% (XVIII).

Example 7

This example illustrates the production of extremely high yields of (XVI) utilizing the process of this invention.

A 300 mL autoclave was charged with acetamide (5.9 g, 0.1 mole), 95% paraformaldehyde (6.8 g, 0.22 mole), water (6.45 g, 0.36 mole), acetic acid (10.6 g, 0.18 mole, 0.12 g/mL of DME), DME (90 mL), and $Co_2(CO)$ (2.0 g, 0.0058 mole) and pressurized to 1500 psi (10,345 kPa) $CO:H_2$ (95:5) at 25° C. This mixture was heated to 125° C. for 30 min. HPLC analysis of the reaction gave a 99% yield of (XVI) and 1% (XVIII).

Example 8

This example illustrates the preparation of (XVI) in the presence of reduced levels of cobalt catalyst.

An autoclave was charged with acetamide (VII)(11.8 g, 0.2 mole), 95% paraformaldehyde (13.6 g, 0.43 mole), water (12.9 g, 0.72 mole), acetic acid (16.8 g, 0.28 mole, 0.19 g/mL of DME), DME (90 mL), and $Co_2(CO)_8$ (2.1 g, 0.006 mole) and pressurized to 2500 psi (17,240 kPa) $CO:H_2$ (95:5) at 25° C. This mixture was heated to 125° C. for 30 min. HPLC analysis of this stream gave a 97% yield of (XVI), 1% (XIV), and 0.5% (XVIII).

Example 9

This example illustrates one way in which a cobalt (II) salt can be recovered for recycle from the carboxy-methylation reaction mixture.

A distillation apparatus was charged with a (XVI) reaction stream represented by Example 2. Once the bottoms temperature of 90° C. was maintained, a distillate with a vapor temperature of 85° C. was collected in a receiving flask. At this time, anhydrous DME was added to the distillation pot at a rate similar to the removal of the 85° C. distillate. After removal of 115 g of 85° C. distillate and addition of 120 g DME, a pink precipitate Co(N-acetyliminodiacetic acid)$_2$ was present in the distillation pot. This solid was isolated by filtration. Analysis of the filtrate revealed that it contained 13 ppm cobalt, implying that 99.8% of the cobalt was removed from the reaction stream.

Example 10

This example illustrates how a catalyst precursor can be regenerated from a cobalt(II) salt and used in the reaction step to give high yields of (XVI).

An autoclave was charged with cobalt acetate tetrahydrate (26.85 g, 0.108 mole) and acetic acid (106 g, 1.77 mole) and pressurized to 2200 psi (15,170 kPa) CO:H$_2$ (90:10) at 25° C. This mixture was heated to 130° C. for 5 h. Gas uptake indicated that approximately 55% of the cobalt(II) salt had been converted to catalyst precursor.

The regenerated catalyst precursor was transferred, under CO:H$_2$ pressure, into the autoclave containing CO:H$_2$ (95:5) at 800 psi (5517 kPa), acetamide (VII) (29.5 g, 0.5 mole), 95% paraformaldehyde (34.0 g, 1.08 mole), water (32.2 g, 1.79 mole), and DME (650 mL). A CO:H$_2$ (95:5) atmosphere at 1500 psi (10,345 kPa) was immediately established. This mixture was heated to 100° C. The reaction warmed to 125° C. and was maintained at this temperature for one hour. HPLC analysis of this stream gave a 95% yield of (XVI), 2% (XIV), 2.5% (XVIII), and 0.5% N-methyliminodiacetic acid.

Example 11

This example illustrates how a cobalt(II) salt can be regenerated and used in the reaction step to give (XVI).

An autoclave was charged with cobalt acetate tetrahydrate (40.0 g, 0.158 mole), Co$_2$(CO)$_8$ (4.1 g, 0.012 mole) and acetic acid (102 g, 1.70 mole) and pressurized to 2200 psi (15,170 kPa) CO:H$_2$ (90:10) at 25° C. This mixture was heated to 130° C. for one hour. Gas uptake indicated that approximately 55% of the cobalt(II) salt had been converted to catalyst precursor.

The regenerated catalyst precursor was transferred under CO:H$_2$ pressure, into the autoclave at 95° C. containing CO:H$_2$ (95:5) at 900 psi (6,210 kPa), acetamide (VII) (59.0 g, 1.0 mole), 95% paraformaldehyde (68.0 g, 2,16 mole), water (64.5 g, 3.60 mole) and DME (750 mL). A CO:H$_2$ atmosphere (95:5) at 1500 psi (10,345 kPa) was immediately established. This mixture was heated to 125° C. and was maintained at this temperature for one hour. HPLC analysis of this stream gave a 77% yield of (XVI), 4% (XIV), 7.0% (XVIII), and 0.1% N-methyliminodiacetic acid.

Example 12

This example illustrates how a cobalt (II) salt can be regenerated and used in the reaction step to give high yields of (XVI).

An autoclave was charged with cobalt acetate tetrahydrate (40.0 g, 0.158 mole), Co$_2$(CO) 1 (4.1 g, 0.012 mole) and acetic acid (100 g, 1.69 mole) and pressurized to 2200 psi (15,170 kPa) CO:H$_2$ (90:10) at 25° C. This mixture was heated to 130° C. for one hour. Gas uptake indicated that approximately 51% of the cobalt (II) salt had been converted to catalyst precursor.

The regenerated catalyst precursor was transferred under CO:H$_2$ pressure, into the autoclave at 95° C. containing CO:H$_2$ (95:5) at 900 psi (6,210 kPa), acetamide (VII) (59.0 g, 1.0 mole), 95% paraformaldehyde (68.0 g, 2,16 mole), water (64.5 g, 3.60 mole) and DME (600 mL). A CO:H$_2$ atmosphere (95:5) at 2200 psi (15,170 kPa) was immediately established. This mixture was heated to 125° C. and was maintained at this temperature for one hour. HPLC analysis of this stream gave a 95% yield of (XVI), 4% (XIV), 7.0% (XVIII), and 0.1% N-methyliminodiacetic acid.

Example 13

This example illustrates the advantage of conducting the regeneration of a Co(II) salt to an active carboxymethylation catalyst in the presence of an amide.

A 2 L autoclave was charged with acetamide (VII) (128.5 g, 2.2 mole), Co(OAc)$_2$.4H$_2$O (33 g, 0.13 mole), THF (750 mL), and acetic acid (250 mL). After sealing the autoclave, 2200 psi (15,172 kPa) of CO:H$_2$ (70:30) was established at 25° C. with stirring at 2000 rpm. The contents of the autoclave were heated to 130° C. and 3200 psi (22,069 kPa) CO:H$_2$ (70:30) was established. After approximately 10 min., rapid gas uptake was observed indicative of the regeneration of the cobalt (II) salt.

Figure 3:
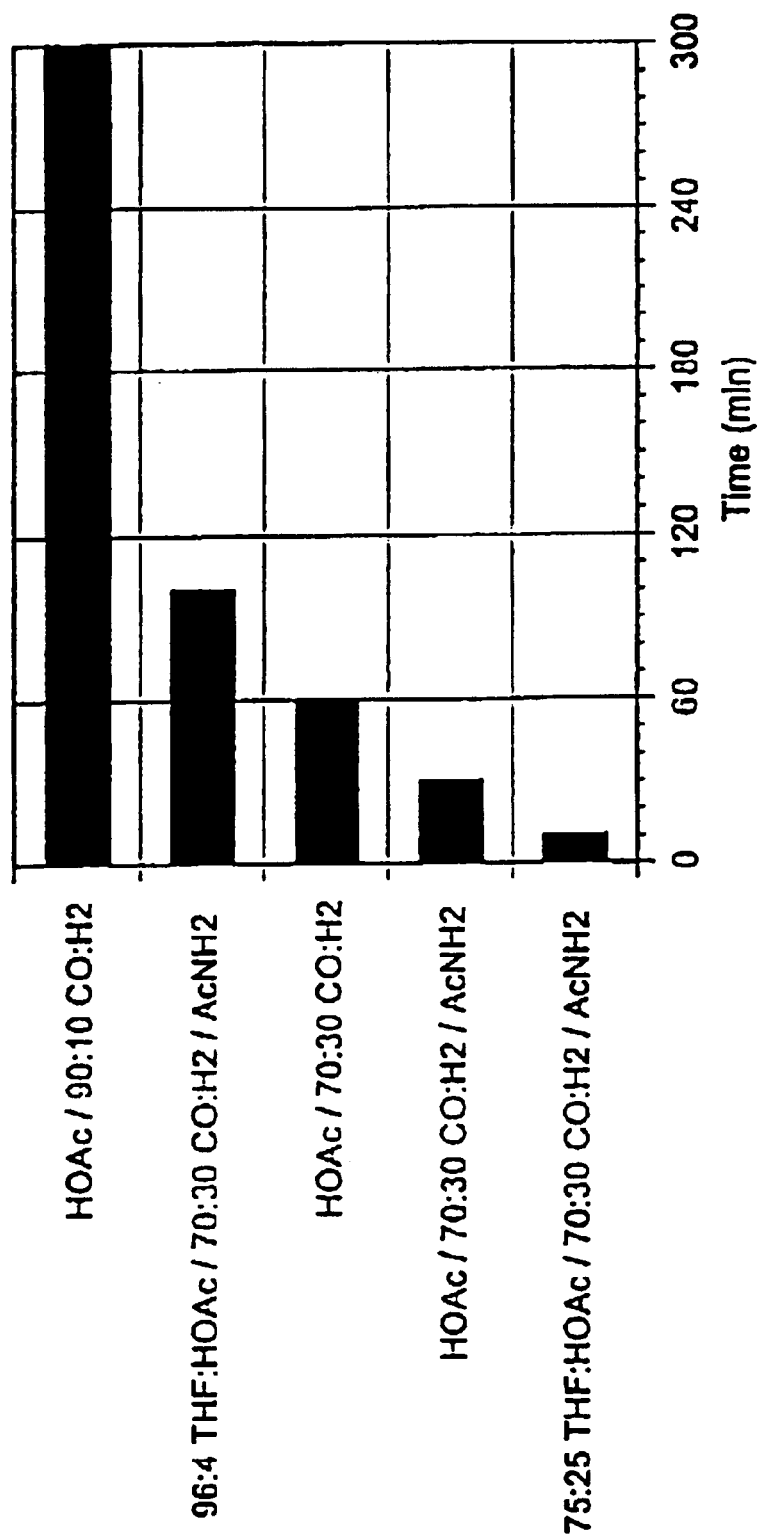
FIG. 3 is a graph of the time required to regenerate a cobalt (II) salt under five separate sets of reaction conditions in which the partial pressure ratio of carbon monoxide to hydrogen is decreased, and the concentrations of acetamide (AcNH2) and acetic acid (HOAc) are varied under the conditions described in Example 13.

For comparison purposes, this procedure was repeated four times except that in one, a 90:10 CO:H$_2$ partial pressure ratio was used in the absence of acetimide and in 1,000 mL acetic acid (no THF) to yield (top bar), 960 ml THF and 40 mL acetic acid (second bar down); third, no THF, no acetimide; fourth bar down, no THF. The advantage of having added amide during the regeneration is further illustrated in FIG. 3, which shows the tremendous increase in the rate of regeneration that is achieved in the presence of added amide compared to examples where no amide is added.

Example 14

This example illustrates the conversion of a variety of different cobalt(II) salts to an active carboxymethylation catalyst mixture in the presence of added amide.

A) A 2 L autoclave was charged with acetamide (VII) (128.5 g, 2.2 mole), Co(II) stearate (83 g, 0.13 mole), and acetic acid (1 L). After sealing the autoclave, 2200 psi (15,172 kPa) of CO:H$_2$ (70:30) was established at 25° C. with stirring at 2000 rpm. The contents of the autoclave were heated to 130° C. and 3200 psi (22,069 kPa) CO:H$_2$ (70:30) was established. After approximately 10 min., rapid gas uptake was observed.

B) A 2 L autoclave was charged with acetamide (VII) (128.5 g, 2.2 mole), cobalt (II) acetylacetonate (34 g, 0.13 mole), and acetic acid (1 L). After sealing the autoclave, 2200 psi (15,172 kPa) of CO:H$_2$ (70:30) was established at 25° C. with stirring at 2000 rpm. The contents of the autoclave were heated to 130° C. and 3200 psi (22,069 kPa) CO:H$_2$ (70:30) was established. After approximately 17 min., rapid gas uptake was observed.

C) A 2 L autoclave was charged with acetamide (VII) (128.5 g, 2.2 mole), cobalt(II) bis-N-acetyliminodiacetate (48.4 g, 0.12 mole), and acetic acid (1 L). After sealing the autoclave, 2200 psi (15,172 kPa) of CO:H$_2$ (70:30) was established at 25° C. with stirring at 2000 rpm. The contents of the autoclave were heated to 130° C. and 3200 psi (22,069 kPa) CO:H$_2$ (70:30) was established. After approximately 20 min., rapid gas uptake was observed.

Example 15

These examples illustrate how different amides can be used in the process of this invention.

A) A 2 L autoclave was charged with urea (V) (60 g, 1.0 mole), Co(OAc)$_2$.4H$_2$O (66 g, 0.26 mole), and acetic acid (1 L). After sealing the autoclave, 2200 psi (15,172 kPa) of CO:H$_2$ (70:30) was established at 25° C. with stirring at 2000 rpm. The contents of the autoclave were heated to 130° C. and 3200 psi (22,069 kPa) CO:$H_2$ (70:30) was established. After approximately one hour, rapid gas uptake was observed. The reaction mass was cooled to 85° C. and the feed gas was changed to a CO:$H_2$ (90:10) composition. Under a constant 3200 psi (22,069 kPa), 47 Wt. % formalin (320 mL, 5.28 mole) was delivered at 16 mL/min. The reaction was stirred at 85° C. for 90 min. after the formalin addition was complete. Then the reaction was cooled to 25° C., removed from the autoclave, and concentrated to an oil under reduced pressure. The oil was treated with 2 L of 10% HCl at 100° C. for two hours. This resulted in a 13% yield of (XIV) and 5% glycine.

B) A 2 L autoclave was charged with methylene bisacetamide (VI) (130 g, 1.0 mole), Co(OAc)$_2$.4$H_2$O (49 g, 0.20 mole), and THF (1 L). After sealing the autoclave, 2200 psi (15,172 kPa) of CO:$H_2$ (70:30) was established at 25° C. with stirring at 2000 rpm. The contents of the autoclave were heated to 130° C. and 3200 psi (22,069 kPa) CO:$H_2$ (70:30) was established. After approximately 0.5 h, rapid gas uptake was observed. Under a constant 3200 psi (22,069 kPa), 47 Wt. % formalin (300 mL, 4.95 mole) was delivered at 10 mL/min. The reaction was stirred at 130° C. for 60 min. after the formalin addition was complete. Then the reaction was cooled to 25° C., removed from the autoclave and assayed. A 62% yield of (XVI) was observed.

C) A 1 L autoclave was charged with N-methylacetamide (IX) (160 g, 2.2 mole), Co(OAc)$_2$.4$H_2$O (33 g, 0.13 mole), and acetic acid (1 L). After sealing the autoclave, 2200 psi (15,172 kPa) CO:$H_2$ (70:30) was established at 25° C. with stirring at 2000 rpm. The contents of the autoclave were heated to 130° C. and 3200 psi (22,069 kPa) CO:$H_2$ (70:30) was established. After approximately 0.5 h, rapid gas uptake was observed. The reaction mass was cooled to 85° C. Under a constant 3200 psi (22,069 kPa), 47 Wt. % formalin (180 mL, 2.97 mole) was delivered at 6 mL/min. The reaction was stirred at 85° C. for 30 min. after the formalin addition was complete. Then the reaction was cooled to 25° C., removed from the autoclave, and assayed for N-acetylsarcosine. This resulted in a 92% yield of (XX).

D) A 1 L autoclave was charged with N-methylacetamide (IX) (90 g, 1.23 mole), Co(OAc)$_2$.4$H_2$O (16.5 g, 0.13 mole), and tetrahydrofuran (500 mL). After sealing the autoclave, 2200 psi (15,172 kPa) of CO:$H_2$ (70:30) was established at 25° C. with stirring at 2000 rpm. The contents of the autoclave were heated to 130° C. and 3200 psi (22,069 kPa) CO:$H_2$ (70:30) was established. After approximately one hour, rapid gas uptake was observed. The reaction mass was cooled to 65° C. and the pressure was slowly reduced to 1500 psi (10,345 kPa). At this point carbon monoxide was established as the carboxymethylation feed gas. Under a constant 1500 psi (10,345 kPa), 47 Wt. % formalin (180 mL, 2.97 mole) was delivered at 6 mL/min. The reaction was stirred at 65° C. for 30 min. after the formalin addition was complete. Then the reaction was cooled to 25° C., removed from the autoclave, and assayed for N-acetylsarcosine (XX). This resulted in an 85% yield of (XX).

E) A 2 L autoclave was charged with 1,3-dimethylurea (X) (96.9 g, 1.1 mole), Co(OAc)$_2$.4$H_2$O (33 g, 0.13 mole), and acetic acid (500 mL). After sealing the autoclave, 2200 psi (15,172 kPa) CO:$H_2$ (70:30) was established at 25° C. with stirring at 2000 rpm. The contents of the autoclave were heated to 130° C. and 3200 psi (22,069 kPa) CO:$H_2$ (70:30) was established. After approximately 1 h, rapid gas uptake was observed. The reaction mass was cooled to 85° C. Under a constant 3200 psi (22,069 kPa), 47 Wt. % formalin (201 mL, 3.31 mole) was delivered at 6 mL/min. The reaction was stirred at 85° C. for 60 min. after the formalin addition was complete. Then the reaction was cooled to 25° C., removed from the autoclave, and concentrated to an oil under reduced pressure. The oil was treated with 2 L of 10% HCl at 100° C. for two hours. This resulted in a 5% yield of (XXIII).

F) A 1 L autoclave was charged with bis-(phosphonomethyl)urea (XII) (12.3 g, 0.05 mole), Co(OAc)$_2$.4$H_2$O (2.4 g, 0.01 mole), and acetic acid (300 mL). After sealing the autoclave, 2200 psi (15,172 kPa) CO:$H_2$ (70:30) was established at 25° C. with stirring at 2000 rpm. The contents of the autoclave were heated to 130° C. and 3200 psi (22,069 kPa) CO:$H_2$ (70:30) was established. After approximately 1.5 h, rapid gas uptake was observed. The reaction mass was cooled to 95° C. Under a constant 3200 psi (22,069 kPa), 47 Wt. % formalin (10 mL, 0.17 mole) was delivered at 0.5 mL/min. The reaction was stirred at 95° C. for 60 min. after the formalin addition was complete. Then the reaction was cooled to 25° C., removed from the autoclave, and concentrated to an oil under reduced pressure. The oil was treated with 500 mL of 10% HCl at 100° C. for two hours. This resulted in a 5% yield of glyphosate (I).

G) A 300 mL autoclave was charged with N-acetylglycine (XVIII)(23.4 g, 0.20 mole), 95% paraformaldehyde (6.8 g, 0.22 mole), water (6.5 g, 0.36 mole), acetic acid (16.8 g, 0.28 mole), DME (90 mL), and Co$_2$(CO)$_8$ (2.01 g, 0.006 mole) and pressurized to 1500 psi (10,345 kPa) CO:$H_2$ (95:5) at 25° C. This mixture was heated to 110° C. for 30 min. HPLC analysis of this stream gave an 87% yield of (XVI), 1.0% (XIV), and 10% unreacted (XVIII).

H) A 2 L autoclave was charged with 130 g of a solid with a composition of 85% methylene bisacetamide (VI)/10% [CH$_3$C(O)N(H)CH$_2$]$_2$NC(O)CH$_3$/5% acetamide (VII), Co(OAc)$_2$.4$H_2$O (49 g, 0.20 mole), and THF (1 L). After sealing the autoclave, 2200 psi (15,172 kPa) of CO:$H_2$ (70:30) was established at 25° C. with stirring at 2000 rpm. The contents of the autoclave were heated to 130° C. and 3200 psi (22,069 kPa) CO:$H_2$ (70:30) was established. After approximately 0.5 h, rapid gas uptake was observed. Under a constant 3200 psi (22,069 kPa), 47 Wt. % formalin (300 mL, 4.95 mole) was delivered at 10 mL/min. The reaction was stirred at 130° C. for 60 min. after the formalin addition was complete. Then the reaction was cooled to 25° C. and removed from the autoclave. HPLC analysis of the reaction indicated a 58% yield of (XVI).

I) A 2 L autoclave was charged with acetamide (VII) (128.5 g, 2.2 mole), Co(OAc)$_2$.4$H_2$O (33 g, 0.13 mole), THF (960 mL), and acetic acid (40 mL). After sealing the autoclave, 2200 psi (15,172 kPa) of CO:$H_2$ (70:30) was established at 25° C. with stirring at 2000 rpm. The contents of the autoclave were heated to 130° C. and 3200 psi (22,069 kPa) CO:$H_2$ (70:30) was established. After approximately 75 min., rapid gas uptake was observed. The contents of the autoclave were cooled to 85° C. and 3200 psi (22,069 kPa) was established with a CO:$H_2$ (90:10) feed. Under a constant 3200 psi (22,069 kPa) (90:10/CO:$H_2$ feed), 47 Wt. % formalin (320 mL, 5.28 mole) was delivered at 9 mL/min. The reaction was stirred at 85° C. for 60 min. after the formalin addition was complete. Then the reaction was cooled to 25° C., removed from the autoclave, and assayed for N-acetyliminodiacetic acid. This resulted in a 85% yield of (XVI) and 3% yield of (XVIII).

Example 16

This example illustrates one preferred mode of conducting the carboxymethylation reaction where the formaldehyde is introduced in a controlled fashion.

A 2 L autoclave was charged with acetamide (VII) (129.8 g, 2.2 mole), THF (1 L), and acetic acid (45 g) and was purged with argon for 10 min. Under the argon purge, Co$_2$(CO)$_8$ (20.9 g, 0.06 mole) was added. After sealing the autoclave, 150 psi (1034 kPa) of CO:$H_2$ (95:5) was estab lished at 25° C. and was slowly vented. Then 2200 psi (15,172 kPa) of CO:$H_2$ (95:5) was established at 25° C. with stirring at 2000 rpm. The contents of the autoclave were heated to 100° C. and 3200 psi (22,069 kPa) CO:$H_2$ (95:5) was established. Under a constant 3200 psi (22,069 kPa), 47 Wt. % formalin (320 mL, 5.28 mole) was delivered at 40 mL/min. The reaction was stirred at 100° C. for 52 min. after the formalin addition was complete. Then the reaction was cooled to 25° C., removed from the autoclave, and assayed for N-acetyliminodiacetic acid. This resulted in a 95% yield of (XVI) and 1% glycine.

Examples 17–19

Examples 17–19 illustrate the profound effect the amount of water present in the reaction has on (XVI) yield. Example 17 contains no water; Example 18 contains 0.36 mole water; Example 19 contains 0.60 mole water.

Example 17

A 300 mL autoclave was charged with acetamide (VII) (11.8 g, 0.2 mole), 95% paraformaldehyde (13.6 g, 0.43 mole), acetic acid (10.6 g, 0.18 mole, 0.12 g/mL of DME), DME (90 mL) and $Co_2(CO)_8$ (4.1 g, 0.012 mole) and pressurized to 1500 psi (10,345 kPa) CO:$H_2$ (95:5) at 25° C. This mixture was heated to 125° C. for 30 min. HPLC analysis of this stream indicated a 30% yield of (XVI) and a 47% yield of (XVIII).

Example 18

A 300 mL autoclave was charged with acetamide (VII) (11.8 g, 0.2 mole), 95% paraformaldehyde (13.6 g, 0.43 mole), water (6.5 g, 0.36 mole), acetic acid (16.8 g, 0.28 mol, 0.19 g/mL of DME), DME (90 mL) and $Co_2(CO)_8$ (4.1 g, 0.012 mole) and pressurized to 1500 psi (10,345 kPa) CO:$H_2$ (95:5) at 25° C. This mixture was heated to 125° C. for 30 min. HPLC analysis of this stream gave a 93% yield of (XVI), 1% (XIV), and 4% (XVIII).

Example 19

A 300 mL autoclave was charged with acetamide (VII) (11.8 g, 0.2 mole), 95% paraformaldehyde (13.6 g, 0.43 mole), water (10.8 g, 0.60 mole), acetic acid (16.8 g, 0.28 mole, 0.19 g/mL of DME), DME (90 mL) and $Co_2(CO)_8$ (4.1 g, 0.012 mole) and pressurized to 1500 psi (10,345 kPa) CO:$H_2$ (95:5) at 25° C. This mixture was heated to 125° C. for 30 min. HPLC analysis of this stream indicated a 91% yield of (XVI), 1% (XIV), and 3% (XVIII).

Example 20

This example illustrates the use of acetonitrile as a solvent.

A 300 mL autoclave was charged with acetamide (VII) (11.8 g, 0.2 mole), 95% paraformaldehyde (13.6 g, 0.43 mole), water (12.9 g, 0.72 mol), acetic acid (16.8 g, 0.28 mole), acetonitrile (90 mL) and $Co_2(CO)_8$ (4.1 g, 0.012 mole) and pressurized to 3200 psi (22,069 kPa) CO:$H_2$ (95:5) at 25° C. This mixture was heated to 110° C for 30 min. HPLC analysis of this stream indicated a 96% yield of (XVI), 1% (XIV), and 3% (XVIII).

Example 21

This example illustrates the use of acetone as a solvent.

A 300 mL autoclave was charged with acetamide (VII) (11.8 g, 0.2 mole), 95% paraformaldehyde (13.6 g, 0.43 mole), water (12.9 g, 0.72 mole), acetic acid (2.1 g, 0.035 mole), acetone (90 mL) and $Co_2(CO)_8$ (2.1 g, 0.006 mol) and pressurized to 3200 psi (22,069 kPa) CO:$H_2$ (95:5) at 25° C. This mixture was heated to 110° C. for 30 min. HPLC analysis of this stream indicated a 95% yield of (XVI), 0.5% (XIV), and 4.5% (XVIII).

Example 22

This example illustrates the utility of various reaction conditions for the carboxymethylation of acetamide (VII). Reactions were run in a fashion similar to Example 1. Summarized in Table 5 are the reaction conditions employed and the results of those reactions. A 300 mL autoclave was charged with 95% paraformaldehyde such that the paraformaldehyde to acetamide mole ratio was 2.15, 90 mL of solvent, and the indicated amounts of acetamide, water, $Co_2(CO)_8$ and acetic acid. The autoclave was pressurized to the indicated pressure with CO:$H_2$ (95:5) at 25° C. Each mixture was heated to 125° C. for 30 min. Analyses were by HPLC. In the table, "DME" is dimethoxyethane, "THF" is tetrahydrofuran and "HOAc" is acetic acid.

TABLE 5

Percent yield of (XVI) based on starting amount of acetamide (VII) under different reaction conditions.

| Example No. | Pressure (psi) | Moles (VII) | Solvent | Water (g) | Moles $Co_2(CO)_8$ | Moles HOAc | % Yield (XVI) |
|---|---|---|---|---|---|---|---|
| 22.01 | 1500 | 0.4 | DME | 25.8 | 0.0112 | 0.28 | 18 |
| 22.02 | 1500 | 0.4 | DME | 25.8 | 0.0226 | 0.28 | 47 |
| 22.03 | 1500 | 0.2 | DME | 12.9 | 0.0168 | 0.177 | 94 |
| 22.04 | 1500 | 0.2 | DME | 12.9 | 0.0119 | 0.28 | 94 |
| 22.05 | 1500 | 0.2 | DME | 12.9 | 0.0116 | 0 | 90 |
| 22.06 | 1500 | 0.2 | DME | 12.9 | 0.0116 | 0.177 | 93 |
| 22.07 | 1500 | 0.2 | DME | 12.9 | 0.0115 | 0.353 | 81 |
| 22.08 | 1500 | 0.2 | DME | 12.9 | 0.0114 | 0.3 | 98 |
| 22.09 | 1500 | 0.2 | DME | 12.9 | 0.0113 | 0.317 | 81 |
| 22.10 | 1500 | 0.2 | DME | 12.9 | 0.0111 | 0.088 | 92 |
| 22.11 | 1500 | 0.2 | DME | 12.9 | 0.0093 | 0.28 | 72 |
| 22.12 | 1500 | 0.2 | DME | 12.9 | 0.0083 | 0.133 | 68 |
| 22.13 | 1500 | 0.2 | DME | 12.9 | 0.0056 | 0.088 | 48 |
| 22.14 | 1500 | 0.2 | DME | 12.9 | 0.0056 | 0.177 | 44 |
| 22.15 | 1500 | 0.2 | DME | 10.8 | 0.0114 | 0.177 | 93 |
| 22.16 | 1500 | 0.2 | DME | 6.5 | 0.0114 | 0.28 | 60 |
| 22.17 | 1500 | 0.2 | DME | 4.3 | 0.0114 | 0.28 | 70 |
| 22.18 | 1500 | 0.2 | DME | 0 | 0.0113 | 0.28 | 30 |
| 22.19 | 1500 | 0.2 | Dioxane | 12.9 | 0.0114 | 0.177 | 21 |
| 22.20 | 1500 | 0.1 | DME | 6.45 | 0.0056 | 0.177 | 99 |
| 22.21 | 2200 | 0.4 | DME | 25.8 | 0.0236 | 0.28 | 56 |
| 22.22 | 2200 | 0.2 | DME | 12.9 | 0.0107 | 0.353 | 95 |
| 22.23 | 2500 | 0.2 | THF | 12.9 | 0.0114 | 0.28 | 92 |
| 22.24 | 2500 | 0.2 | DME | 12.9 | 0.0032 | 0.28 | 81 |
| 22.25 | 2500 | 0.2 | DME | 12.9 | 0.0061 | 0.28 | 99 |
| 22.26 | 2500 | 0.2 | Dioxane | 12.9 | 0.0113 | 0.28 | 95 |
| 22.27 | 3200 | 0.2 | Dioxane | 12.9 | 0.0031 | 0.07 | 2 |
| 22.28 | 3200 | 0.2 | Dioxane | 12.9 | 0.0059 | 0.28 | 34 |
| 22.29 | 3200 | 0.2 | HOAc | 12.9 | 0.0112 | 1.552 | 45 |
| 22.30 | 3200 | 0.2 | THF | 12.9 | 0.0062 | 0.07 | 98 |
| 22.31 | 3200 | 0.2 | THF | 12.9 | 0.0062 | 0.21 | 99 |
| 22.32 | 3200 | 0.2 | THF | 12.9 | 0.0035 | 0.072 | 97 |
| 22.33 | 3200 | 0.2 | THF | 12.9 | 0.0033 | 0 | 88 |
| 22.34 | 3200 | 0.2 | THF | 12.9 | 0.0031 | 0.28 | 95 |
| 22.35 | 3200 | 0.2 | THF | 12.9 | 0.003 | 0.035 | 88 |
| 22.36 | 3200 | 0.2 | THF | 12.9 | 0.0029 | 0.14 | 94 |
| 22.37 | 3200 | 0.2 | THF | 12.9 | 0.0017 | 0.035 | 6 |
| 22.38 | 3200 | 0.4 | DME | 25.8 | 0.0234 | 0.57 | 83 |

Example 23

The tables contained in this example illustrate how certain combinations of reaction conditions result in extremely high yields of (XVI).

TABLE 6

Percent yield of (XVI) based on starting amount of acetamide (VII) when HOAc/Co ratio is varied against moles $H_2O$. Reaction conditions included 1500 psi (10,345 kPa) $CO:H_2$ (95:5), 90 mL DME solvent, 11.8 g acetamide, 13.6 g of 95% paraformaldehyde, and 4.1 g $Co_2(CO)_8$. Parenthetical values represent Example Numbers from Table 5.

| | HOAc/Co Molar Ratio[a] | | | | | | | |
|---|---|---|---|---|---|---|---|---|
| Moles $H_2O$ | 15.179 | 15.55 | 23.607 | 24.585 | 24.645 | 24.828 | 26.214 | 27.941 |
| 0 | | | | | | 30 (22.18) | | |
| 0.239 | | | | 70 (22.17) | | | | |
| 0.361 | | | | | 60 (22.16) | | | |
| 0.600 | | 93 (22.15) | | | | | | |
| 0.717 | 93 (22.06) | | 94 (22.04) | | | | 98 (22.08) | 81 (22.09) |

[a]Calculated using the number of moles of Co atoms (supplied in the reaction as $Co_2(CO)_8$).

TABLE 7

Percent yield of (XVI) based on starting amount of acetamide (VII) when mmoles of acetic acid (HOAc) are varied against mmoles of $Co_2(CO)_8$. Reaction conditions included 1500 psi (10,345 kPa) $CO:H_2$ (95:5), 90 mL DME solvent, 12.9 g water, 13.6 g of 95% paraformaldehyde, and 11.8 g acetamide. Parentetical values represent Example Numbers from Table 5.

| | mmol $Co_2(CO)_8$ | | | | | | | | | | |
|---|---|---|---|---|---|---|---|---|---|---|---|
| Mmol HOAc | 5.6 | 5.7 | 8.3 | 9.3 | 11.1 | 11.3 | 11.4 | 11.5 | 11.6 | 11.9 | 16.8 |
| 0 | | | | | | | | | 90 (22.05) | | |
| 88 | | 48 (22.13) | | 92 (22.10) | | | | | | | |
| 133 | | | 68 (22.12) | | | | | | | | |
| 177 | 44 (22.14) | | | | | | | | 93 (22.06) | | 94 (22.03) |
| 280 | | | | 72 (22.11) | | | | | | 94 (22.04) | |
| 300 | | | | | | | 98 (22.08) | | | | |
| 317 | | | | | | 81 (22.09) | | | | | |
| 353 | | | | | | | | 81 (22.07) | | | |

TABLE 8

Percent yield of (XVI) based on acetamide (VII) when acetic acid (HOAc) is varied against $Co_2(CO)_8$. Reaction conditions include: 3200 psi (22,069 kPa) $CO:H_2$ (95:5), 90 mL THF solvent, 12.9 g water, 13.6 g of 95% paraformaldehyde, and 11.8 g acetamide. Values in parenthesis represent example numbers from Table 5.

| | Mmol $Co_2(CO)_8$ | | | | | | |
|---|---|---|---|---|---|---|---|
| Mmol HOAc | 1.7 | 2.9 | 3.0 | 3.1 | 3.3 | 3.5 | 6.2 |
| 0 | | | | | 88 (22.33) | | |
| 35 | 6 | | 88 | | | | |

TABLE 8-continued

Percent yield of (XVI) based on acetamide (VII) when acetic acid (HOAc) is varied against $Co_2(CO)_8$. Reaction conditions include: 3200 psi (22,069 kPa) $CO:H_2$ (95:5), 90 mL THF solvent, 12.9 g water, 13.6 g of 95% paraformaldehyde, and 11.8 g acetamide. Values in parenthesis represent example numbers from Table 5.

| | Mmol $Co_2(CO)_8$ | | | | | | |
|---|---|---|---|---|---|---|---|
| Mmol HOAc | 1.7 | 2.9 | 3.0 | 3.1 | 3.3 | 3.5 | 6.2 |
| 70 | (22.37) | | (22.35) | | | | 98 (22.30) |
| 72 | | | | | 97 (22.32) | | |
| 140 | | 94 (22.36) | | | | | |
| 210 | | | | | | | 99 (22.31) |
| 280 | | | | 95 (22.34) | | | |

Example 24

This example illustrates the effect of pressure on the yields of (XVI) in the presence of acetic acid.

TABLE 9

Reaction conditions included $CO:H_2$ (95:5), 90 mL DME solvent, 12.9 g water, acetic acid-to-cobalt ratio of about 15:1 (based on cobalt atoms), 13.6 g of 95% paraformaldehyde, and 11.8 g acetamide. Example numbers refer to examples from Table 5.

| Example No. | Pressure (psi) | Mole % Cobalt in Reaction Mixture | % Yield NAIDA |
|---|---|---|---|
| 22.14 | 1500 | 6 | 44 |
| 22.25 | 2500 | 6 | 99 |
| 22.07 | 1500 | 12 | 81 |
| 22.22 | 2200 | 12 | 95 |

Example 25

This example illustrates how increasing the pressure in the carboxymethylation reactions allows for dramatic increase in yield at higher reaction payloads.

TABLE 10

Effect of pressure on percent yield of (XVI) at various acetamide payload concentration. Reaction conditions included 1500 or 3200 psi (22,069 kPa) $CO:H_2$ (95:5), 90 mL DME solvent, 3.6 molar ratio of water-to-acetamide, about 15.0 molar ratio of acetic acid-to-cobalt atoms, and 13.6 g of 95% paraformaldehyde. Example numbers refer to examples from Table 5.

| Example No. | Pressure Psi | Acetamide/DME (g/6) | % Yield NAIDA |
|---|---|---|---|
| 22.38 | 3200 | 0.31 | 83 |
| 22.02 | 1500 | 0.31 | 47 |
| 22.07 | 1500 | 0.15 | 81 |
| 22.20 | 1500 | 0.075 | 99 |

Example 26

This example illustrates the effect that various solvents have on the yield of (XVI).

TABLE 11

Reaction conditions included $CO:H_2$ (95:5), 90 mL solvent, 0.2 moles acetamide, 12.9 g water, and 13.6 g of 95% paraformaldehyde. Example numbers refer to examples from Table 5.

| Example No. | Solvent | Pressure (psi) | mmol $Co_2(CO)_8$ | mmol HOAc | % Yield NAIDA |
|---|---|---|---|---|---|
| 22.19 | Dioxane | 1500 | 11.4 | 177 | 21 |
| 22.06 | DME | 1500 | 11.6 | 177 | 93 |
| 22.27 | Dioxane | 3200 | 3.1 | 70 | 2 |
| 22.32 | DME | 3200 | 3.5 | 72 | 97 |

Example 27

This example illustrates how cobalt(II) bis-N-acetyliminodiacetate can be recovered from a typical carboxymethylation reaction mixture.

A) A 144.07 g quantity of a final carboxymethylation reaction mass was generated in a process similar to that described in Example 1. An autoclave was charged with acetamide (11.8 g, 0.2 mole), 95% paraformaldehyde (13.6 g, 0.43 mole), water (12.9 g, 0.72 mol), acetic acid (33.0 g, 0.55 mole), acetone (70 g), and $Co_2(CO)_8$ (2.55 g, 0.007 mole) After sealing the autoclave, 150 psi (1034 kPa) of $CO:H_2$ (95:5) was established at 25° C. and was slowly vented. Then, 2200 psi (15,172 kPa) $CO:H_2$ (95:5) was established at 25° C. with stirring at 2000 rpm. The contents of the autoclave were heated to 100° C. and 3200 psi (22,069 kPa) $CO:H_2$ (95:5) was established. This mixture was heated to 100° C. for 30 min. Of this reaction mass, 141.3 g were transferred to a round bottom flask. Air was bubbled through the stirred reaction mass at room temperature for 130 min. until the solution turned dark purple with a slight cloudiness. The air supply was then turned off and the reaction mixture was heated at reflux for 80 min. Pink precipitate started to appear after 30 min. of heating and continued through the heating period. The system was cooled to 30° C. and the pink solid was filtered, washed with acetone, and dried to give 5.89 g of solid. Analysis showed the solid to contain 13.7% cobalt and 79.87% N-acetyliminodiacetic acid. Analysis of the liquid filtrate showed 242 ppm cobalt and 22.64% N-acetyliminodiacetic acid. Of the cobalt, 96.7% was in the pink solid and 3.3% was in the filtrate.

B) A 149.00 g quantity of a final carboxymethylation reaction mass was generated in a process similar to that described in Example 1. An autoclave was charged with acetamide (11.8 g, 0.2 mole), 95% paraformaldehyde (13.6 g, 0.43 mole), water (12.9 g, 0.72 mol), acetic acid (33.0 g, 0.55 mol), acetone (70.1 g), and $Co_2(CO)_8$ (3.03 g, 0.009 mole). After sealing the autoclave, 150 psi (1034 kPa) $CO:H_2$ (95:5) was established at 25° C. and was slowly vented. Then, 2200 psi (15,172 kPa) of $CO:H_2$ (95:5) was established at 25° C. with stirring at 2000 rpm. The contents of the autoclave were heated to 100° C. and 3200 psi (22,069 kPa) $CO:H_2$ (95:5) was established. This mixture was heated to 100° C. for 30 min. Of this reaction mass, 143.9 g was transferred to a round bottom flask. Air was bubbled through the stirred reaction mass while it was brought to 61.5° C. It was held there for 120 min. while air bubbling continued. The solution was clear and dark red to purple after 40 min. and pink precipitate first appeared after 60 min. The system was cooled to 30° C. and the pink solid was filtered off, washed with acetone, and dried to give 6.59 g solid. Analysis of the solid showed 13.4% cobalt and 78.97% N-acetyliminodiacetic acid. Analysis of the liquid filtrate showed 215 ppm cobalt and 20.63% N-acetyliminodiacetic acid. Of the cobalt, 97.2% was in the pink solid and 2.8% was in the filtrate.

C) In a typical carboxymethylation reaction, a 300 mL autoclave was charged with a mixture of water (12.9 g), glacial acetic acid (33.0 g), acetone (90 mL), paraformaldehyde (13.6 g of 95+% powder), acetamide (11.8 g), and $Co_2(CO)_8$ (4.109 g, equivalent to ca. 1416 mg cobalt). A gas mixture of $CO:H_2$ (95:5) was charged at an initial pressure of 3200 psi (22,069 kPa), the reactor was heated to 110° C. for 30 min. with stirring, and then cooled to below 20° C. The pressure was slowly vented, the system purged with nitrogen ($N_2$), and the reactor was sealed up. The contents were heated with stirring (closed system) to 90° C., stirred at 90° C. for 3 h, and then cooled to 20° C. The pressure in the reactor, after cooling, was 160 psi (1103 kPa). The pressure was released, the reactor opened, and the contents filtered to obtain 8.44 g of pink powder containing 11.8% cobalt (996 mg; 70% of cobalt used). The mother liquors were found to contain 203 mg cobalt. Some solids adhered to the reactor. These were removed by dissolution in water and found to contain 267 mg of cobalt.

D) In a typical carboxymethylation reaction, a 300 mL autoclave was charged with a mixture of water (12.9 g), glacial acetic acid (33.0 g), tetrahydrofuran (90 mL), paraformaldehyde (13.6 g of 95+% powder), acetamide (11.8 g), and $CO_2(CO)_8$ (2.078 g, equivalent to ca. 716 mg cobalt). A gas mixture of $CO:H_2$ (95:5) was charged at an initial pressure of 3200 psi (22,069 kPa), the reactor heated to 110° C. for 30 min. with stirring, and then cooled to below 20° C. The pressure was slowly vented, the system purged with $N_2$, and the reactor was opened under an inert atmosphere and its contents transferred to a 250 mL glass three-necked round bottom flask fitted with a gas inlet tube, a thermocouple thermometer, and a distillation head. The vessel was heated under a $N_2$ atmosphere and the contents distilled (pot temp.—70–80° C., still head temp—64° C.) until ca. 60 mL distillate was collected. Pink precipitate formed in the bottoms during the distillation. After cooling, the bottoms were filtered to obtain 4.96 g of pink powder containing 12.0% cobalt (596 mg; 83% of cobalt used). The mother liquors were found to contain 13 mg cobalt. Some solids adhered to the distillation flask. These were removed by dissolution in water and found to contain 37 mg of cobalt.

Example 28

This example illustrates the conversion of (XVI) to a mixture of (XVII) under various reaction conditions.

N-acetyliminodiacetic acid (XVI) monohydrate (45 g) and varying amounts of water and acetic acid were heated at 175° C. or 195° C. for various periods of time. After cooling to room temperature, the mixture was filtered. The solid was washed with water (10 mL) and dried to give 1,4-di(carboxymethyl)-2,5-diketopiperazine. The table below shows the yields of solid under various conditions.

TABLE 12

| Ex. | Temp. (C) | Time (min) | Added water (g) | Added acetic acid (g) | Total DKP (XVII) (g) | Total IDA (XIV) (g) | Isolated DKP (XVII) (g) | Isolated IDA (XIV) (g) |
|---|---|---|---|---|---|---|---|---|
| 28.1 | 175 | 90 | 0 | 10 | 22.98 | 0.85 | 22.66 | 0.00 |
| 28.2 | 175 | 20 | 0 | 10 | 19.26 | 1.76 | 19.02 | 1.21 |
| 28.3 | 175 | 45 | 0 | 0 | 23.71 | 0.69 | 23.40 | 0.00 |
| 28.4 | 175 | 20 | 5 | 10 | 18.66 | 3.37 | 18.25 | 2.52 |
| 28.5 | 195 | 45 | 0 | 10 | 23.98 | 0.36 | 23.56 | 0.00 |
| 28.6 | 195 | 45 | 5 | 0 | 24.78 | 0.29 | 24.04 | 0.00 |
| 28.7 | 195 | 45 | 5 | 10 | 23.74 | 0.83 | 23.31 | 0.00 |
| 28.8 | 195 | 20 | 5 | 10 | 23.15 | 0.92 | 22.69 | 0.00 |
| 28.9 | 195 | 5 | 5 | 10 | 21.29 | 1.23 | 20.83 | 0.00 |

Example 29

This example illustrates that the amount of either (XVII) or (XIV) obtained from (XVI) can vary depending on the reaction conditions.

N-acetyliminodiacetic acid (XVI) monohydrate (10 g), acetic acid (5 g), and water (35 g) were heated to 150° C. in an autoclave. Table 13 shows the relative amounts of products based on $^1H$ NMR analysis at various times.

TABLE 13

| Hours | % NAIDA (XVI) | % DKP (XVII) | % IDA (XIV) |
|---|---|---|---|
| 0 | 100 | 0 | 0 |
| 0.5 | 35 | 8 | 57 |
| 2 | 6 | 19 | 74 |
| 4 | 5 | 27 | 68 |

Example 30

This example illustrates the conversion of N-acetyliminodiacetic acid (XVI) to iminodiacetic acid (XIV) in the presence of a mineral acid.

A) N-acetyliminodiacetic acid (XVI) monohydrate (8.45 g) and 9 N HCl (119) were heated under reflux for 30 min. Analysis of the mixture showed 99% conversion to iminodiacetic acid hydrochloride. After cooling, the mixture is filtered and the solid is dried to give iminodiacetic acid hydrochloride.

B) A mixture of 30% $H_2SO_4$, 30% $H_2O$ and 40% NAIDA XVI (by weight) was heated in a 110° C. oil bath for 20 min. Analysis of the mixture showed that hydrolysis to iminodiacetic acid (XIV) was complete.

Example 31

This example illustrates the preparation of N-(phosphonomethyl)iminodiacetic acid (XV) from N-acetyliminodiacetic acid (XVI) monohydrate.

N-acetyliminodiacetic acid (XVI) monohydrate, sulfuric acid, water, and phosphorus acid were heated to 110° C. and 42% formalin (6.5 mL, 0.10 mole) was added over a one hour period. After another 1.75 hours at 110° C. the mixture was cooled and filtered. The solid was washed and dried to give N-(phosphonomethyl)iminodiacetic acid (PMIDA). All reactants/solvents appear in the table below along with the amount of PMIDA (XV) produced. Unless otherwise noted, the amount of $H_3PO_3$ is 11.39 g (0.14 mole)

TABLE 14

Phosphonomethylations of (XVI)

| NAIDA (XIV) 92% (g) | $H_2CO$, ca. 42% (mL) | $H_2SO_4$ 98% (g) | $H_2O$ (g) | Wet Solid (g) | PMIDA (XV) (g) |
|---|---|---|---|---|---|
| 17.5 | 8.60 | 10 | 10 | 23.90 | 22.09 |
| 17.5 | 8.60 | 15 | 10 | 22.23 | |
| 17.4 | 3.64 | 15 | 25 | 21.43 | 19.36 |
| 17.4 | 8.60 | 10 | 10 | 20.55 | 18.79 |
| 17.4 | 8.60 | 15 | 5 | 21.65 | 16.17 |
| 19.0 | 6.50 | 15 | 5 | 25.43 | 20.37 |
| 17.0 | 5.85 | 15 | 5 | 21.45 | 15.09 |
| 17.0 | 5.85 | 15 | 5 | 14.98 | 12.46 |
| 19.0 | 5.85 | 15 | 5 | 18.37 | 14.47 |
| 19.0 | 4.85 | 15 | 5 | 15.71 | 13.19 |

Example 32

This example illustrates the preparation (XV) from 1,4-di(carboxymethyl)-2,5-diketopiperazine (XVII).

A) 1,4-di(carboxymethyl)-2,5-diketopiperazine (XVII) (0.8059 g), water (0.51 g), 12N HCl (4.25 g) and 47.4% formalin (0.5342 g) were heated in a sealed tube in a 105° C. oil bath with stirring for one hour then heated at 105° C. for one hour to yield 55% of (XV).

B) 1,4-di(carboxymethyl)-2,5-diketopiperazine (11.9 g), phosphorus trichloride hydrolysate (43.8% $H_3PO_3$, 16.8% HCl, 26 g) and 20% HCl (26 g) were heated to 120° C. and formalin (8.4 g, 47.42%) was added over a 30 min. period. The solution was held at 120° C. for 1.75 h to yield 88.2% of (XV).

Example 33

This example illustrates the direct preparation of (I) from (XVIII).

A 1 L flask was charged with N-acetylglycine (XVIII) (117.0 g, 1.0 mole), acetic acid (100 mL), and water (18 g, 1.0 mole). Phosphorus trichloride(137 g, 1.0 mole) was slowly added at 25° C. with rapid stirring. The temperature of the reaction mass quickly warmed to 50° C. during this time. Then at 45° C., 47 Wt. % formalin (60 mL, 1.03 mole) was added over 0.5 h. The solution was maintained at 75° C. for 19 h after the addition of formalin. Assay of the reaction at this time indicated a 15% yield of glyphosate (I).

Example 34

This example illustrates the conversion of (XVII) to (XIV) in the presence of mineral acid under various conditions.

1,4-di(carboxymethyl)-2,5-diketopiperazine (XVII) (1 g) was heated under reflux in aqueous 1N, 3N, 6N, 9N, and 12N HCl. The table below shows the percent of (XVII) remaining at various times. The hydrolysis product was shown by NMR to be mostly (XIV).

TABLE 15

Percent (XVII) Remaining

| Min. | 12N | 9N | 6N | 3N | 1N |
|---|---|---|---|---|---|
| 5 | 80.12 | | 86.49 | 93.71 | 100 |
| 10 | 67.07 | 89.11 | 84.95 | 94.7 | 98.96 |
| 20 | 58.7 | 70.74 | 72.51 | 87.94 | 98.77 |
| 40 | 36.65 | 56.25 | 64.25 | 87.14 | 98.65 |
| 80 | 22.36 | 32.1 | 46.1 | 79.01 | 98.62 |
| 160 | 9.93 | 14.44 | 29.03 | 78.92 | 98.79 |
| 320 | | 3.25 | 5.13 | 68.95 | 97.13 |
| 640 | | | | 37.39 | 97.36 |
| 1280 | | | | 24 | |
| 2720 | | | | 5.96 | |
| 6970 | | | | | 75.78 |

Example 35

These examples illustrate the conversion of (XX) to (XXI).

A) N-acetyl sarcosine (XX) (20.0 g, 152.5 mmole), phosphorous acid (12.59, 152.4 mmole), and concentrated HCl (37.6 g) were mixed and refluxed in a 120° C. oil bath. Formalin, 37% (13.6 g, 167.6 mmole) was added dropwise over 20 min. and the reaction was continued for an additional 19 h. HPLC analysis indicated a-99% yield of N-methylglyphosate (XXI) based on moles of (XX) charged.

B) Per conditions described in (A), N-propionylsarcosine (20.0 g, 137.8 mmole) was converted into N-methylglyphosate using phosphorous acid (11.3 g, 137.8 mmole), concentrated hydrochloric acid (10.0 g), and 12.3 g of 37% formalin (152.1 mmole). HPLC analysis indicated a 96.6% yield of N-methylglyphosate (XXI) based on moles of N-propionylsarcosine charged.

C) Per conditions described in (A), sarcosine anhydride (XXV) (2.06 g, 14.50 mmole) was converted into N-methylglyphosate (XXI) using phosphorous acid (2.38 g, 29.02 mmole), concentrated hydrochloric acid (5.7 g), and 2.6 g of 37% formalin (32.0 mmole). HPLC analysis indicated a 97.2% yield of (XXI) based on mmoles of (XXV) charged.

D) N-acetyl sarcosine (XX)(2.0 g, 15.3 mmole), phosphorous acid (1.25 g, 15.3 mmole) were mixed with concentrated sulfuric acid (3.1 g) and water (1.7 g) then refluxed in a 120° C. oil bath. Formalin, 37% (1.4 g, 16.7 mmole) was added dropwise over 20 min. and the reaction was continued for an additional 18 h. $^{31}P$ NMR analysis indicated 98% yield of (XXI) based on mmoles of (XX) charged.

Example 36

This example illustrates the conversion of sarcosine (XXIII) to (XXI).

Sarcosine (XXIII) (89.09 g, 1.00 mole), phosphorous acid (82.0 g, 1.0 mole) and concentrated hydrochloric acid (110 g) were mixed and refluxed in a 130° C. oil bath. Formalin, 37% (89.3 g, 1.1 mole) was added dropwise over 20 min. and the reaction was continued for an additional 85 min. At this point, 31P NMR indicated the following product distribution (on a molar basis): N-methyl glyphosate (89.9%), phosphorous acid (2.1%), phosphoric acid (1.9%), hydroxymethyl phosphorous acid (0.4%), and an unknown product (5.7%; NMR: triplet, 8.59 ppm). After cooling to room temperature, 40 g (1 mole) sodium hydroxide was added followed by 250 g water leading to the formation of a white precipitate which was recovered by filtration and assayed by HPLC. The total recovered yield of N-methylglyphosate was 70.5% based on the amount of sarcosine and phosphorous acid used.

Example 37

This example illustrates the conversion of an N-methylglyphosate (XXI) to glyphosate (I) using a platinum catalyst and oxygen.

A) N-methylglyphosate (XXI) (10.0 g), 140 g water, and 1 g platinum black (Aldrich Chemical) were combined in a round bottom flask and equipped with a water-cooled reflux condenser immersed in a 150° C. oil bath. Oxygen was bubbled through the reaction mixture for four hours as the solution was stirred. At the end of this period, HPLC analysis revealed the following product distributions (on a molar basis): glyphosate (I) (86.4%), N-methylglyphosate (XXI) (8.7%), aminomethylphosphonic acid (2.2%) and phosphoric acid (2.7%). Glyphosate (I) precipitated from the solution after cooling to room temperature.

B) A mixture of N-methylglyphosate (XXI) (10.0 g), platinum black (2.0 g) and sufficient water to bring the total volume of the mixture to 200 ml, was stirred for two hours and 40 min. at a temperature of 80° C. while oxygen at a pressure of 1 atm. was bubbled through the reaction mixture. Analysis of the reaction mixture indicated the following product distribution (on a molar basis): N-methylglyphosate (XXI)— not detected; glyphosate (I) (85.4%); phosphoric acid (8.1%). The other components of the reaction mixture were unidentified.

Example 38

This example illustrates the conversion of N-isopropylglyphosate to glyphosate (I) using a platinum (Pt) catalyst and oxygen.

N-isopropylglyphosate (1.0 g), 10 g water, and 0.3 g platinum black (Aldrich) were combined in a round bottom flask equipped with a water-cooled reflux condenser and immersed in an 80° C. oil bath. A stream of oxygen was introduced at the reaction surface for 18 hours as the solution was stirred. At the end of this period, $^{31}$P NMR indicated the following product distribution (on a molar basis): glyphosate (I) (91%), amino phosphonic acid (1%), phosphoric acid (6%), and an unknown product (2%; 15.0 ppm). Glyphosate (I) precipitated from solution after cooling to room temperature.

Example 39

Cobalt Precipitation by Anaerobic Oxidation—Reflux Method

In a typical carboxymethylation reaction, a 300-mL autoclave was charged with a mixture of distilled deionized water (12.9 g), glacial acetic acid (33.0 g), tetrahydrofuran (90 mL), paraformaldehyde (13.6 g of 95+% powder), acetamide (11.8 g), and cobalt tetracarbonyl dimer (2.105 g, equivalent to ca. 726 mg Co). A gas mixture of 95:5 CO:H2 was charged at an initial pressure of 3200 psi, the reactor was heated to 110° C. for 30 minutes with stirring, and then cooled to below 20° C. The pressure was slowly vented, the system purged with N2, and the reactor was opened under an inert atmosphere and its contents transferred to a 250-mL glass 3-necked round-bottomed flask fitted with a gas inlet tube, a thermocouple thermometer, and a distillation head. The vessel was heated at reflux under a N2 atmosphere for 3 hours. Pink precipitate formed during heating. After cooling, the mixture was filtered to obtain 5.62 g of pink powder containing 12.6% cobalt (708 mg; 98% of cobalt used). The mother liquors were found to contain 13 mg cobalt (2% of cobalt used).

Example 40

This example illustrates the improved selectivities which may be achieved in the oxidative dealkylation of an N-alkyl amino acid reaction product when an electroactive molecular species is adsorbed to a noble metal catalyst. All of the electroactive molecular species adsorbed to platinum black in this example undergo oxidation and reduction by electron transfer. Thus, the treatment of platinum-containing catalysts by both electroactive molecular species and their oxidative precursors is exemplified herein.

This experiment was conducted by heating to reflux a mixture containing 1 g of N-(phosphonomethyl)-N-methylglycine XXI ("NMG"), 20 ml water, and 50 mg of platinum metal in a magnetically-stirred, round-bottom flask equipped with a reflux condenser. Oxygen was bubbled through for 5 hours using a needle. The catalyst was then removed by filtration and the filtrate analyzed by HPLC.

To prepare the organic-treated catalysts, 0.5 g of platinum black (Aldrich Chemical Co., Inc., Milwaukee, Wis.) was added to a solution of 25 mg of the poison (i.e., the electroactive molecular species) in 50 ml of anhydrous acetonitrile. The mixture sat capped in an Erlenmeyer flask for four days, except that the 4,4'-difluorobenzophenone catalyst only was exposed to solution for one day. The catalyst subsequently was recovered by filtration, rinsed with acetonitrile and diethyl ether, and air-dried overnight.

The 2,4,7-trichlorofluorene catalyst was prepared using 0.3 g of Pt black and 30 ml of a solution consisting of 834.5 ppm 2,4,7-trichlorofluorene in acetonitrile/1% $CH_2Cl_2$ solution (used to facilitate dissolution of the electroactive molecular species) which was allowed to evaporate at room temperature. The catalyst subsequently was washed with ethanol and air-dried.

The inorganic-treated catalysts were prepared by combining 0.50 g of Pt black, 50 ml of tetrahydrofuran, and either 25 or 100 mg of the inorganic electroactive molecular species, and stirring overnight at room temperature in a sealed 125 ml Erlenmeyer flask. The catalyst was recovered by filtration, washed with diethyl ether, and air-dried overnight.

The inorganic species used, all of which are available from Aldrich Chemical (Milwaukee, Wis.), were:

1. 5,10,15,20-tetrakis(pentafluorophenyl)-21H,23H-porphine iron (III) chloride (abbreviated "Fe(III)TPFPP chloride" in Table 16). Approximately 25 mg was used to prepare the catalyst.
2. 5,10,15,20-tetraphenyl-21H,23H-porphine iron (III) chloride (abbreviated "Fe(III) TPP chloride" in Table 16). Approximately 25 mg was used to prepare the catalyst.
3. 5,10,15,20-tetraphenyl-21H,23H-porphine nickel (II) (abbreviated as "Ni(II) TPP" in Table 16). Approximately 25 mg was used to prepare the catalyst.
4. Ruthenium-tris (2,2'-bipyridine) dichloride (abbreviated as "[Ru(bpy)$_3$]Cl$_2$" in Table 16). Approximately 100 mg was used to prepare the catalyst.

5 Ferrocene. Approximately 100 mg was used to prepare the catalyst.

Where available, literature data on the oxidation potential ($E_{1/2}$) of the electroactive molecular species is reported in Table 16. This example illustrates that electroactive molecular species being relatively soluble in water (e.g., ferrocene and [Ru(bpy)$_3$]Cl$_2$) are less effective at enhancing glyphosate selectivity. This example also demonstrates that hydrophobic electroactive molecular species increase the catalyst's selectivity. Electroactive molecular species having oxidation potentials more negative than about +0.3 V vs SCE generally decrease conversion. Thus, the preferred electroactive molecular species for enhancing the selectivity and conversion of NMG oxidation may be either organic or inorganic, but should be hydrophobic and have oxidation potentials more positive than about 0.3 volts vs. SCE.

tive molecular species: N-hydroxyphthalimide and triphenylmethane.

These catalysts were used to oxidize N-isopropyl glyphosate by the method described in the previous example. Approximately 1 g of N-isopropyl glyphosate was substituted for N-(phosphonomethyl)-N-methyl-glycine XXI. The results shown in Table 17 demonstrate that electroactive molecular species improve the selectivity of platinum on carbon catalysts for this reaction. Modifiers with less positive oxidation potentials such as triphenylmethane appear to be more effective than those with more positive oxidation potentials, such as N-hydroxyphthalimide. This example also demonstrates that the use of graphitic supports for platinum is less effective in suppressing undesired side reactions in N-isopropyl glyphosate oxidations than is the case for N-(phosphonomethyl)-N-methyl-glycine XXI.

TABLE 16

Use of Electroactive Molecular Species on NMG Oxidation

| Poison | $E_{1/2}$ V vs SCE | Conv. (%) | Glyphosate Select (%) | MAMPA Select (%) | $H_3PO_4$ Select (%) |
|---|---|---|---|---|---|
| None | — | 45.7 | 83.1 | 9.0 | 7.95 |
| 2,4,7-trichlorofluorene | ? | 52.9 | 93.5 | 2.5 | 4.0 |
| N-hydroxyphthalimide | +1.44 | 56.3 | 93.2 | 2.4 | 4.4 |
| tris(4-bromophenyl)amine | +1.05 | 35.3 | 93.5 | 2.5 | 4.0 |
| TEMPO | +0.6 | 71.2 | 92.9 | 2.4 | 4.6 |
| Triphenylmethane | +0.27 | 22.1 | 93.4 | ~0 | 6.6 |
| 4,4'-difluorobenzophenone | ? | 8.6 | 91.4 | ~0 | 10.9 |
| Fe(III)TPFPP chloride | +0.07 | 22.9 | 89.7 | 4.0 | 6.3 |
| Fe(III)TPP chloride | +1.11 | 69.3 | 91.1 | 2.6 | 6.3 |
| Ni(II)TPP | +1.15 | 53.8 | 90.3 | 2.9 | 6.8 |
| [Ru(bpy)$_3$]Cl$_2$ | +1.32 | 37.9 | 68.9 | 12.1 | 19.1 |
| Ferrocene | +0.307 | 70.8 | 82.6 | 6.0 | 11.4 |

TABLE 17

Use of Electroactive Molecular Species During Oxidation of N-Isopropyl Glyphosate

| Catalyst | $E_{1/2}$ V vs SCE | Conv. (%) | Glyphosate Select (%) | MAMPA Select (%) | $H_3PO_4$ Select (%) |
|---|---|---|---|---|---|
| Platinum black | — | 77.0 | 79.8 | 8.9 | 11.3 |
| 20% Pt/Vulcan XC-72R carbon (25 mg used) | +0.07 | 81.9 | 20.5 | 72.1 | 7.4 |
| 20% Pt/Vulcan treated with N-hydroxyphthalimide loading 35.3 mg/g (26 mg used) | +1.44 | 41.2 | 31.6 | 62.1 | 6.2 |
| 20% Pt/Vulcan treated with triphenylmethane loading 305 mg/g (32.6 mg used) | +0.27 | 60.2 | 50.1 | 25.4 | 24.5 |

Example 41

This example illustrates the effect of electroactive molecular species on the platinum-catalyzed oxidation of N-isopropyl glyphosate using the commercially available catalyst 20% Pt on Vulcan XC-72R carbon (manufactured by Johnson-Matthey and available from Alfa/Aesar (Ward Hill, Mass.). The commercial catalyst was tested along with a catalyst which had been impregnated with two electroac- Example 42

This example demonstrates the selectivities that may be achieved when N-alkyl glyphosates are oxidized at low rates of oxygen delivery and moderate conversion if an electroactive molecular species such as TEMPO (i.e., 2,2,6,6-tetramethyl piperidine N-oxide) is added to the reaction mixture. No pretreatment of the catalyst is required. This example further demonstrates that the conversion improves over the first few cycles when the electroactive molecular species is added to the mixture. Finally, this example demonstrates that the electroactive molecular species reduces the amount of noble metal loss.

A 300 ml glass pressure bottle was equipped with a thermocouple and two fritted filters. One of the filters located about half an inch above the center of the bottom of the bottle was used for gas dispersion. The second filter, located about an inch from the bottom and not centered, was used for the withdrawal of liquids. A gas exit line leading to a back pressure regulator set to maintain the pressure at 50 psig also was provided. Approximately 60 g of N-(phosphonomethyl)-N-methyl-glycine XXI, 180 ml of water, 3 g of platinum black (Aldrich Chemical, Milwaukee, Wis.), and 40 mg of TEMPO dissolved in 1 ml of acetonitrile were combined in the pressure reactor. The mixture was heated to 125EC while stirring under a 50 psig nitrogen atmosphere, forming a homogeneous mixture. A nitrogen/oxygen mixture (75% nitrogen, 25% oxygen by volume) was bubbled through for 90 minutes at a flow rate of 1 slpm while the pressure was maintained at 50 psig. The reaction mixture then was withdrawn through a fritted filter, leaving the catalyst behind. Another 60 g of N-(phosphonomethyl)-N-methyl-glycine XXI, 180 ml of water, and 40 mg of TEMPO in 1 ml of acetonitrile subsequently was added to the flask and the cycle repeated. Four cycles in all were performed. In all cases, (M)AMPA concentrations were below the quantifiable limits, although traces were detected. The only quantifiable by-product detected was phosphoric acid. The conversions and selectivities at the end of each of the four cycles are shown in Table 18.

The concentration of dissolved platinum was determined at the end of each run by inductively-coupled plasma mass spectrometry. This dissolved platinum concentration was less than 0.1 ppm in cycles 2, 3, and 4. This is lower than the concentration of platinum that was observed (i.e., 0.3 to 1.1 ppm) when platinum black was used without the presence of an electroactive molecular species under similar reaction conditions over 7 cycles. Although a higher amount of platinum leached into solution during the first cycle (i.e., the dissolved platinum was 8.3 ppm), it is believed that most of the lost platinum was primarily unreduced platinum on the platinum black's surface. In fact, the same phenomenon occurred when platinum black was used without an electroactive species; in that instance the concentration of dissolved platinum was 4.2 ppm.

TABLE 18

Oxidation of NMG XXI in the Presence of TEMPO at 125EC for 90 Min.

| Cycle Number | Conversion (%) | Glyphosate Selectivity (%) | $H_3PO_4$ Selectivity (%) |
|---|---|---|---|
| 1 | 32.6 | 98.3 | 1.7 |
| 2 | 38.0 | 98.1 | 1.9 |
| 3 | 43.3 | 98.1 | 1.9 |
| 4 | 46.2 | 97.3 | 2.7 |

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. A compound having the formula:

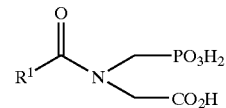

wherein $R^1$ is —$NR^3R^4$; and $R^3$ and $R^4$ are independently hydrogen, hydrocarbyl, or substituted hydrocarbyl.

2. The compound as set forth in claim 1, wherein $R^3$ and $R^4$ are independently hydrogen or hydrocarbyl.

3. The compound as set forth in claim 1, wherein $R^3$ and $R^4$ are independently phosphonomethyl, hydroxymethyl, amidomethyl, carboxymethyl, or an ester or salt of carboxymethyl or phosphonomethyl.

* * * * *